(12) United States Patent
Andres et al.

(10) Patent No.: US 7,186,398 B2
(45) Date of Patent: Mar. 6, 2007

(54) FE/AU NANOPARTICLES AND METHODS

(75) Inventors: Ronald P. Andres, Lafayette, IN (US); Alicia T. Ng, Johor (MY)

(73) Assignee: Purdue Research Foundation, West Lafayette, IN (US)

( * ) Notice: Subject to any disclaimer, the term of this patent is extended or adjusted under 35 U.S.C. 154(b) by 410 days.

(21) Appl. No.: 10/373,609

(22) Filed: Feb. 24, 2003

(65) Prior Publication Data

US 2004/0247924 A1 Dec. 9, 2004

Related U.S. Application Data

(60) Provisional application No. 60/392,192, filed on Jun. 28, 2002, provisional application No. 60/388,221, filed on Jun. 13, 2002, provisional application No. 60/358,983, filed on Feb. 22, 2002.

(51) Int. Cl.
| | |
|---|---|
| *A61K 49/00* | (2006.01) |
| *A61K 51/00* | (2006.01) |
| *B22F 3/00* | (2006.01) |
| *C12Q 1/68* | (2006.01) |
| *C07H 21/00* | (2006.01) |
| *C07H 21/04* | (2006.01) |

(52) U.S. Cl. ............. 424/9.1; 424/1.17; 428/546; 536/26.6; 536/23.1; 536/24.3; 435/6

(58) Field of Classification Search .......... 424/1.17, 424/9.1; 428/546; 536/26.6, 23.1, 25.3; 435/6
See application file for complete search history.

(56) References Cited

U.S. PATENT DOCUMENTS

| | | | |
|---|---|---|---|
| 3,970,518 A | 7/1976 | Giaver | |
| 3,985,649 A | 10/1976 | Eddelman | |
| 4,070,246 A | 1/1978 | Kennedy et al. | |
| 4,115,535 A | 9/1978 | Giaver | |
| 4,123,396 A | 10/1978 | Rembaum et al. | |
| 4,152,210 A | 5/1979 | Robinson et al. | |
| 4,157,323 A | 6/1979 | Yen et al. | |
| 4,169,804 A | 10/1979 | Yapel | |
| 4,177,253 A | 12/1979 | Davies et al. | |
| 4,331,654 A | 5/1982 | Morris | |
| 4,452,773 A | 6/1984 | Molday | |
| 4,454,234 A | 6/1984 | Czerlinski | |
| 4,554,088 A | 11/1985 | Whitehead et al. | |
| 4,628,037 A | 12/1986 | Chagnon et al. | |
| 4,638,032 A | 1/1987 | Benner | |
| 4,695,392 A | 9/1987 | Whitehead et al. | |
| 4,731,337 A | 3/1988 | Luotola et al. | |
| 4,777,145 A | 10/1988 | Luotola et al. | |
| 4,778,594 A | 10/1988 | Doctor | |
| 4,916,081 A | 4/1990 | Kamada et al. | |
| 4,978,610 A | 12/1990 | Forrest et al. | |

(Continued)

FOREIGN PATENT DOCUMENTS

WO  WO 03/072830  9/2003

(Continued)

OTHER PUBLICATIONS

Geerts et al., "Nanovid Tracking: A New Automatic Method for the Study of Mobility in Living Cells Based on Colloidal Gold and Video Microscopy", *Biophys. J.*, 1987;52:775-782.

(Continued)

*Primary Examiner*—Jezia Riley
(74) *Attorney, Agent, or Firm*—Mueting, Raasch & Gebhardt, P.A.

(57) ABSTRACT

A novel nanoscale, metal particle containing Fe atoms and Au atoms in solid solution. The particle is superparamagnetic with a large magnetic susceptibility at room temperature, is resistant to oxidation, and can be readily functionalized for use in diverse applications by attaching organic molecules to its surface.

25 Claims, 9 Drawing Sheets

U.S. PATENT DOCUMENTS

| | | | |
|---|---|---|---|
| 5,091,206 | A | 2/1992 | Wang et al. |
| 5,145,784 | A | 9/1992 | Cox et al. |
| 5,178,947 | A | 1/1993 | Charmot et al. |
| 5,232,782 | A | 8/1993 | Charmot |
| 5,238,810 | A | 8/1993 | Fujiwara et al. |
| 5,238,811 | A | 8/1993 | Fujiwara et al. |
| 5,508,164 | A | 4/1996 | Kausch et al. |
| 5,541,072 | A | 7/1996 | Wang et al. |
| 5,648,124 | A | 7/1997 | Sutor |
| 5,744,367 | A | 4/1998 | Talley et al. |
| 5,807,758 | A | 9/1998 | Lee et al. |
| 5,834,121 | A | 11/1998 | Sucholeiki et al. |
| 5,891,648 | A | 4/1999 | Martin et al. |
| 5,962,218 | A | 10/1999 | Leland et al. |
| 5,998,224 | A | 12/1999 | Rohr et al. |
| 6,013,531 | A | 1/2000 | Wang et al. |
| 6,086,821 | A | 7/2000 | Lee |
| 6,096,563 | A | 8/2000 | Hajizadeh et al. |
| 6,110,660 | A | 8/2000 | Kriz et al. |
| 6,133,043 | A | 10/2000 | Talley et al. |
| 6,133,047 | A | 10/2000 | Elaissari et al. |
| 6,231,760 | B1 | 5/2001 | Siddiqi |
| 6,294,342 | B1 | 9/2001 | Rohr et al. |
| 6,303,316 | B1 | 10/2001 | Kiel et al. |
| 6,517,777 | B2 | 2/2003 | Liljestrand et al. |
| 6,682,584 | B2 | 1/2004 | Pozarnsky et al. |
| 2002/0068187 | A1 | 6/2002 | O'Connor et al. |
| 2002/0072069 | A1 | 6/2002 | Ford et al. |
| 2002/0177143 | A1* | 11/2002 | Mirkin et al. ............. 435/6 |
| 2004/0086885 | A1 | 5/2004 | Lee et al. |

FOREIGN PATENT DOCUMENTS

| | | |
|---|---|---|
| WO | WO 03/073444 | 9/2003 |
| WO | WO 04/003508 | 1/2004 |

OTHER PUBLICATIONS

Kumar et al., "Analysis of mutations in the pore-forming region essential for insecticidal activity of a *Bacillus thuringiensis* δ-endotoxin", *J. Bacteriol.*, 1999, 181:6103-6107.

Welkos et al., "The role of antibodies to *Bacillus anthracis* and anthrax toxin components in inhibiting the early stages of infection by anthrax spores", *Microbiol.*, 2001; 147:1677-1685.

Carpenter et al., "Effects Of Shell Thickness On Blocking Temperatures Of Nanocomposites Of Metal Particles With Gold Shells", *IEEE Transactions of Magnetics*, Sep. 1999, pp. 3496-3498, vol. 35, No. 5.

Lin et al., "Gold-Coated Iron (Fe@Au) Nanoparticles: Synthesis, Characterization, and Magnetic Field-Induced Self-Assembly", *Journal of Solid-State Chemistry*, 2001, pp. 26-31, 159.

Mahoney et al., "Aerosol synthesis of nanoscale clusters using atmospheric arc evaporation", *Materials Science and Engineering*, 1995, pp. 160-164, A204.

Chao et al., "Synthesis of a Supported Metal Catalyst Using Nanometer-Size Clusters", *Journal of Colloid and Interface Science*, 1994, pp. 290-295, 165.

Andres et al., "Self-Assembly of a Two-Dimensional Superlattice of Molecularly Linked Metal Clusters", *Science*, Sep. 20, 1996, pp. 1690-1693, vol. 273.

Baselt et al., "A biosensor based on magnetoresistance technology" *Biosens. Bioelectron.*, 1998; 13:731-9.

Baselt et al., "A high-sensitivity micromachined biosensor" *Proceedings of the IEEE*, 1997;85:672-80.

Baselt et al., "Biosensor based on force microscope technology", *J. Vac. Sci. Technol. B*, 1996;14:789-93.

Bowles et al., "Generation of supported metal clusters of controlled size" *J. Molec. Catalysis*, 1983;20:279-87.

Chen et al., "Gold-coated iron nanoparticles for biomedical applications" *J. Appl. Phys.*, 2003;93:7551-3.

Choi et al., "Unusual thermochromic behavior of photoreactive dyes confined in helical amylose as inclusion complex" *Macromolecules*, 1998;31:9406-8.

Clays et al., "Enhancement of the molecular hyperpolarizability by a supramolecular amylose-dye inclusion complex, studied by hyperrayleigh scattering with fluorescence supression", *Chem. Phys. Lett.*, 1998,293:337-42.

Dabbousi et al. "(CdSe)ZnS core-shell quantum dots: synthesis and chracterization of a size series of highly luminescent nanocrystallites" *J. Phys. Chem. B*, 1997;101:9463-75.

Daniel et al., "Gold nanoparticles: assembly, supramolecular chemistry, quantum-size-related properties, and applications toward biology, catalysis, and nanotechnology" *Chem. Rev.*, 2004;104:293-346.

De Brabander et al., "Probing microtubule-dependent intracellular motility with nanometre particle video ultramicroscopy (nanovid ultramicroscopy)" *Cytobios.*, 1985,43:273-83.

Demers et al., "A fluorescence-based method for determining the surface coverage and hybridization effciency of thiol-capped oligonucleotides bound to gold thin films and nanoparticles", *Anal. Chem.*, 2000;72:5535-41.

Dixit et al., "Synthesis and grafting of thioctic acid-PEG-folate conjugates onto Au nanoparticles for selective targeting of folate receptor-positive tumor cells" *Bioconjug. Chem.*, 2006;17:603-9.

Foos et al., "Thiol-terminated di-, tri-, and tetraethylene oxide functionalized gold nanoparticles: a water-soluble, charge-neutral cluster" *Chem. Mater.*, 2002;14:2401-8.

Goodman et al., "Biomacromolecule surface recognition using nanoparticles" *Mini-Rev. Org. Chem.*, 2004;1:103-14.

Hayat, M.A., *Colloidal Gold: Principles, Methods, and Applications*, Academic Press Inc., San Diego, CA, 1989. Title Page and Table of Contents.

Hohreiter et al., "Cross-correlation analysis for temperature measurement" *Meas. Sci. Technol.*, 2002;13:1072-8.

Jackson et al., "PCR analysis of tissue samples from the 1979 Sverdlovsk anthrax victims: the presence of multiple bacillus anthracis strains in different Victims", *Proc. Natl. Acad. Sci.*, 1998;95:1224-9.

Jain, "Delivery of molecular medicine to solid tumors: lessons from in vivo imaging of gene expression and function" *J. Control. Release*, 2001;41:7-25.

Kim et al., "Solvatochromism of non-linear optical chromophores containing the dithienothiophene group in donor-acceptor molecules", *Chem. Phys. Lett.*, 1996;255:147-50.

Kim et al., "Second harmonic generation by spontaneous self-poling supramolecular thin films of amylose-dye inclusion complex" *J. Am. Chem. Soc.*, 1996;118:12220-1.

Kim et al., "A novel supramolecular self-assembly thin film with spontaneous polar order", *Thin Solid Films*, 1998;327-329:172-5.

Kohler et al., "A bifuntional poly(ethylene glycol) silane immobilized on metallic oxide-based nanoparticles for conjugation with cell targeting agents" *J. Am. Chem. Soc.*, 2004;126:7206-11.

Kucik et al., "Forward transport of glycoproteins on leading lamellipodia in locomoting cells", *Nature*, 1989;340:315-7.

Lee et al., "Implementation of force differentiation in the immunoassay" *Anal. Biochem.*, 2000;287:261-71.

Lee et al., "Direct measurement of the forces between complementary strands of DNA", *Science*, 1994;266:771-3.

Lee et al., "Sensing discrete streptavidin-biotin interactions with atomic force microscopy", *Langmuir*, 1994;10:354-7.

Liu et al., "Guided self-assembly of Au nanocluster arrays electronically coupled to semiconductor device layers" *Appl. Phys. Lett.*, 2000;77:373-5.

Mangeney et al., "Synthesis and properties of water-soluble gold colloids covalently derivatized with neutral polymer monolayers" *J. Am. Chem. Soc.*, 2002;124:5811-21.

Metzger et al., "Development and characterization of surface chemistries for microfabricated biosensors" *J. Vac. Sci. Technol. A*, 1999;17:2623-8.

Mirkin et al., "A DNA-based method for rationally assembling nanoparticles into macroscope materials", *Nature*, 1996;382:607-9.

Mock et al., "Anthrax", *Annu. Rev. Microbiol.*, 2001;55:647-71.

Momet et al., "Magnetic nanoparticle design for medical diagnosis and therapy" *J. Mater. Chem.*, 2004;14:2161-75.

O'Connor et al., "Magnetic properties of FePt$_x$/Au and CoPt$_x$/Au core-shell nanoparticles" *J. Magn. Magn. Mater.*, 2001;226:1915-7.

Patil et al., "The minimum-energy structure of nanometer-scale gold clusters" *Z. Phys. D.*, 1993,26:135-7.

Petty et al., "Characterization of DNA size determination of small fragments by flow cytometry", *Anal. Chem.*, 1995,67:1755-61.

Ravel et al., "Oxidation of iron in iron/gold core shell nanoparticles" *J. Appl. Phys.*, 2002;91:8195-7.

Sambrook et al., *Molecular Cloning: A Laboratory Manual, Books 1-3*, Cold Spring Harbor Laboratory Press, Cold Spring Harbor, NY, 1989; title page, publisher's page and table of contents only (30 pgs).

Santiago et al., "A particle image velocimetry system for microfluidics", *Exp. Fluids*, 1998;25:316-9.

Sonvico et al., "Folate-conjugated iron oxide nanoparticles for solid tumor targeting as potential specific magnetic hyperthermia mediators: synthesis, physicochemical characterization, and in vitro experiments" *Bioconjug. Chem.*, 2005;16:1181-8.

Tatusova, "BLAST 2 sequences, a new tool for comparing protein and nucleotide sequences" *FEMS Microbiol. Lett.*, 1999;174:247-50.

Tokumitsu et al., "Grafting of alkanethiol-terminated poly(ethylene glycol) on gold" *Langmuir*, 2002;18:8862-70.

Tshikhudo et al., "Biocompatible gold nanoparticles" *Mater. Sci. Technol.*, 2004;20:980-4.

Turkevich, J. "A Study of the Nucleation and Growth Processes in the Synthesis of Colloidal Gold" *Discussions of Faraday Soc.* 1951;11:55-75.

Van den Bossche et al., "Synthesis and grafting of folate-PEG-thioctic acid conjugates to Au nanoparticles for selective targeting of cancer cells" Poster Presentation at: Particles 2005- Surface Modification in Particle Technology, San Francisco, CA, Aug. 13-16, 2005.

Zhang et al., "Surface modification of superparamagnetic magnetite nanoparticles and their intracellular uptake" *Biomaterials*, 2002;23:1553-61.

\* cited by examiner

FE/AU NANOPARTICLES AND METHODS

This application claims the benefit of U.S. Provisional Application Ser. Nos. 60/358,983, filed 22 Feb. 2002, 60/388,221, filed 13 Jun. 2002, and 60/392,192, filed 28 Jun. 2002, each of which is incorporated herein by reference in its entirety.

RELATED APPLICATION

This application incorporates by reference U.S. patent application Ser. No. 10/373,600 filed Feb. 24, 2003, entitled Magnetic Nanomaterials and Methods for Detection of Biological Materials.

BACKGROUND OF THE INVENTION

Magnetic materials play an important role in modern telecommunication, computing, and information storage technology. Ultra-small magnetic particles are needed for the manufacture of ferro-fluids, i.e. colloidal suspensions of magnetic particles. Particles that are paramagnetic have applications in magnetic refrigeration, color imaging, and biological detection and separation processes. In particular, paramagnetic microparticles that are functionalized with specific binding moieties are increasingly used for cell separation due to the high efficiency, high cell viability, and low cost of this process and have been proposed for use in various schemes for pathogen detection.

The magnetic particles presently used in ferro-fluid and bio-magnetic applications suffer from a number of deficiencies that limit their utility. These magnetic carriers make use of magnetic iron oxides usually embedded in a polymer matrix. They are not nano-size (typically micron size or larger), are characterized by low magnetic susceptibility that makes them unsuitable for many applications, and are susceptible to loss of their magnetic properties due to chemical transformation of magnetic iron oxides to diamagnetic $Fe_2O_3$.

Metal nanoparticles with their smaller size and higher magnetic susceptibility would be expected to possess a number of advantages over the current commercial particles, especially in bio-magnetic applications. They have a lower surface area which would reduce non-specific protein binding and since many immunological responses rely on surface antigen recognition they would be expected to produce reduced immunological response. Their higher magnetic susceptibility means that smaller magnetic fields would be required to manipulate them.

In many ways the ideal particle for bio-magnetic applications would be a nano-size particle that combines the high magnetic susceptibility of metallic iron with the well developed chemistry for attaching bio-active moieties and the resistance to oxidation of metallic gold. O'Connor and coworkers have reported the microemulsion synthesis of nanoparticles composed of a central core of Fe atoms surrounded by a 2–3 nm thick shell of Au atoms that purport to have these very characteristics (the so-called "Fe@Au particles", J. Solid State Chem. 159, 26–31 (2001); U.S. Pat. Appl. 20020068187, published Jun. 6, 2002). These nanoparticles are synthesized in a two step process in a reverse micelle. If the gold shell perfectly encapsulates the iron core of a Fe@Au particle, the Fe atoms will be protected from oxidation, however, Ravel et al. (J. Appl. Phys. 91, 8195–8197 (2002)) have found that on average most of the Fe atoms in Fe@Au particles are oxidized, most probably due to the imperfect encapsulation of the Fe cores. This results in a lower magnetic susceptibility and non-uniform magnetic properties among a population of Fe@Au particles nominally of a given size and Fe composition. A second drawback of Fe@Au particles for bio-magnetic applications is the difficulty of removing all traces of the surfactant species used in their synthesis and replacing them with selected bio-active moieties without causing aggregation of the nanoparticles. Thus, while the Fe@Au particle represents a substantial advance over current magnetic carriers, there is still a need to improve on the Fe@Au particle for bio-magnetic applications.

There remains a need for improved, readily synthesized nanoscale magnetic particles, especially particles whose magnetic moment can be precisely controlled, and particles that can be readily modified by attachment of selected organic molecules to their surfaces.

SUMMARY OF THE INVENTION

The invention provides a novel nanoscale metal particle. This particle is preferably a binary component particle and contains Fe atoms and Au atoms distributed essentially randomly in a solid solution. The term "essentially randomly," as used herein to describe the spatial arrangement of Fe and Au atoms within the particle, means that the particle exhibits no observable segregation into Fe-rich or Au-rich phases or regions. In a preferred embodiment, the spatial distribution of Fe and Au atoms within the particle is random. The particle is equiaxed with a spherical morphology, and is characterized by a uniform volume magnetization. The particle is preferably superparamagnetic with a magnetic moment proportional to the number of Fe atoms in the nanoparticle. The nanoparticles exhibit strong magnetic susceptibility and stable magnetic characteristics. Under some circumstances the nanoparticles of the invention may exhibit electrical conductivity.

The particles are synthesized as bare metal particles without any associated surfactant species or other organic impurities. They can be readily captured as stable colloidal suspensions in either aqueous or organic solvents. The surface of these bare metal particles is decorated with gold atoms, and they can be readily functionalized with selected bio-active moieties without aggregation.

The nanoparticle, or nanoparticle core as described in more detail below, preferably contains only Fe atoms and Au atoms. In a particularly preferred embodiment, the nanoparticle is characterized by a Fe atom/Au atom ratio that does not exceed about 7:3, i.e. Fe(70)/Au(30); more preferably the Fe atom/Au atom ratio does not exceed about 1:1, i.e., Fe(50)/Au(50).

The Fe/Au nanoparticle of the invention preferably has a diameter ranging from about 5 nm to about 50 nm. The variance in the diameters of a population of Fe/Au nanoparticles is preferably no more than about 50% of the mean, and can be further reduced by means of size-selective precipitation. Both the size and the composition of these so-called Fe/Au nanoparticles can be controlled independently.

In a preferred embodiment, the nanoparticle includes an Fe/Au core optionally functionalized with a plurality of organic molecules linked to the surface of the core. The organic molecules are preferably present as a monolayer on the surface of the Fe/Au core. The organic molecules may be conveniently selected to impart a hydrophobic or hydrophilic character or other properties to the nanoparticle, as desired. For example, the organic molecules used to functionalize the Fe/Au core can be selected so as to render the nanoparticle soluble in an organic solvent or an aqueous environment, and to that end can include a hydrophobic, hydrophilic or amphipathic polymer. Biomolecules can be used to functionalized the nanoparticles for various biological or medical applications; nonlimiting examples include nucleic acids and oligonucleotides, proteins and peptides, carbohydrates, and lipids.

Preferably, the organic molecule attached to the surface of a Fe/Au metal core contains at least one sulfur atom, and the linkage between the organic molecule and the metal core is made through an interaction between Au atoms on the surface of the metal core and sulfur atoms in the organic molecules.

The organic molecule linked to the metal core can provide the desired functionality, or it can serve as a linker molecule. In one such embodiment, the nanoparticle includes a plurality of first organic molecules, such as a hydrophobic or hydrophilic polymer, and as well as a plurality of second organic molecules covalently linked to the first organic molecules. The first organic molecule functions as a chemical linker (the linker molecule) that indirectly links the second organic molecule (the functionalizing molecule) to the metal core. The linker molecule contains at least one first active group capable of binding to the surface of the nanoparticle (nanoparticle binding group), and at least one second active group capable of binding to the functionalizing molecule. The first and second active groups are separated by a spacer region, which in one embodiment is a polymer but is not limited to any particular molecule. Preferred nanoparticle binding groups are those that can covalently interact with the Fe/Au nanoparticle of the invention and include amines, phosphines, especially sulfur containing groups such as thiols, disulfides, dithiocarbamates, dithiophosphates, dithiophosphonates, thioethers, thiosulfates, and thioureas. Preferably, the linker molecule contains sulfur and is linked to the metal core via an interaction between the sulfur atom and the Au atoms on the metal core surface. Examples of suitable linker molecules can be found, for example, in U.S. Pat. Appl. 20020072069 (published Jun. 13, 2002).

In another aspect, the invention provides a biological material that includes the nanoparticle of the invention. The nanoparticle can be bound covalently or noncovalently to the biological material. Nonlimiting examples of a biological material include an organelle, a membrane and a cell.

In yet another aspect, the invention provides a population of superparamagnetic nanoparticles having uniform magnetic moments, such that the nanoparticles align their magnetic moments within an external magnetic field.

The invention thus further includes a method for making the novel Fe/Au nanoparticles. The nanoparticles of the invention are preferably prepared in a gas phase synthesis by first evaporating a metal charge including Fe atoms and Au atoms using an atmospheric pressure direct current arc discharge to yield a metal vapor (Mahoney at al., Materials Sci. & Eng. 204:160–164 (1995)). The metal vapor is contacted with a forced convective flow of argon gas to control particle nucleation and growth, yielding solid metal nanoparticles having Fe atoms and Au atoms distributed therein. Preferably the spatial distribution of Fe atoms and Au atoms in the nanoparticle is essentially random or random. The nanoparticles are cooled by contact with a forced convective flow helium or nitrogen gas.

Finally, the cooled nanoparticles are bubbled through a liquid to yield a colloidal suspension of magnetic nanoparticles. The liquid is preferably an aqueous solution or an organic solvent such as mesitylene containing molecules that attach to the surface of the particles. Capturing the nanoparticles in a liquid and protecting them with a solvent-derived molecular layer (see Chao and Andres, *J. of Colloid and Interface Sci.* 165, 290 (1994)) prevents them from aggregating and creates a stable suspension, i.e., a nanocolloid.

The invention also includes methods for using the novel Fe/Au nanoparticles. The magnetic Fe/Au nanoparticle of the invention has numerous applications in the fabrication of nanoelectronic devices and materials including nanocomposites, nanowires, nanoelectronic networks and circuits; in the manufacture of ferro-fluids; and in biotechnology. The particle is superparamagnetic and may, in some embodiments, have one or more advantages the following advantages, including but not limited to:

1) The particles are metallic, have a high degree of magnetization and a large magnetic susceptibility.
2) Because the surface of the particle contains a high density of gold atoms, a wide variety of organic molecules can be attached to the surface to impart colloidal stability or to link the particles to each other through the use of the well studied binding reaction of thiols and disulfides to gold surfaces. The particles can also be functionalized with a wide variety of biological moieties.
3) The presence of the Au atoms also protects the Fe atoms in the interior of the particle from oxidation.
4) The particle exhibits a uniform volume magnetization and, because the particle does not contain layers, shells or regions having different compositions, it can be synthesized as a truly nanoscale particle, i.e. a particle whose diameter is only a few nanometers. These particles are so small that they can function as "magnetic molecules" in certain biological applications.
5) The particles are superparamagnetic at room temperature, i.e. the unpaired electron spins due to the Fe atoms in the particle are coupled together to produce a net magnetic moment. The orientation of this magnetic moment is random in the absence of an external magnetic field. In the presence of an external magnetic field the magnetic moment aligns with the field
6) The magnetic moment of the Fe/Au particles is proportional to the number of Fe atoms in the particle. It can be varied independent of the particle diameter by varying the ratio of Fe to Au. For example at 293K, for 10 nm diameter Fe(50)/Au(50) nanoparticles the net saturation magnetic moment is ~1 Bohr magneton per Fe atom in the particle or 22.5 emu/g.
7) The particles can be synthesized with a uniform particle diameter and a uniform atomic composition. The particle diameter can be accurately controlled in the range of about 5 nm to about 50 nm. The Fe atom concentration can be accurately controlled in the range of about 5 atom % to about 50 atom % (i.e., a range of about Fe(5)/Au(95) to about Fe(50)/Au(50)
8) The particles are stable against oxidation and can be functionalized so that they are soluble in either organic solvents (i.e. they can be made hydrophobic) or water (i.e. they can be made hydrophilic).
9) The nanoparticles are expected to be nontoxic. The nanoparticle or nanoparticle core consists of only Fe atoms and Au atoms which are generally considered to be biocompatible. In addition, the immunogenicity of the Fe/Au nanoparticles is expected to be low. Since many immunological responses rely on surface antigen recognition, the small size and surface area of the Fe/Au nanoparticles are expected to limit non-specific protein binding and hence the host's immunological response.

DETAILED DESCRIPTION OF ILLUSTRATIVE EMBODIMENTS

Fe/Au Nanoparticle Production

The nanoparticles of the invention are produced in a distributed arc cluster source (DACS). This is an updated version of the aerosol reactor first proposed by Mahoney and Andres (Materials Science and Engineering A204, 160–164 (1995)). This new apparatus is designed to produce colloidal suspensions of metal nanoparticles having diameters in the 5–50 nm size range. The DACS is a gas aggregation reactor, which employs forced convective flow of an inert gas to control particle nucleation and growth. It is capable of producing equiaxed nanoparticles of almost any metal or metal mixture with a fairly narrow size distribution and is capable of achieving gram per hour production rates.

Figure 1:
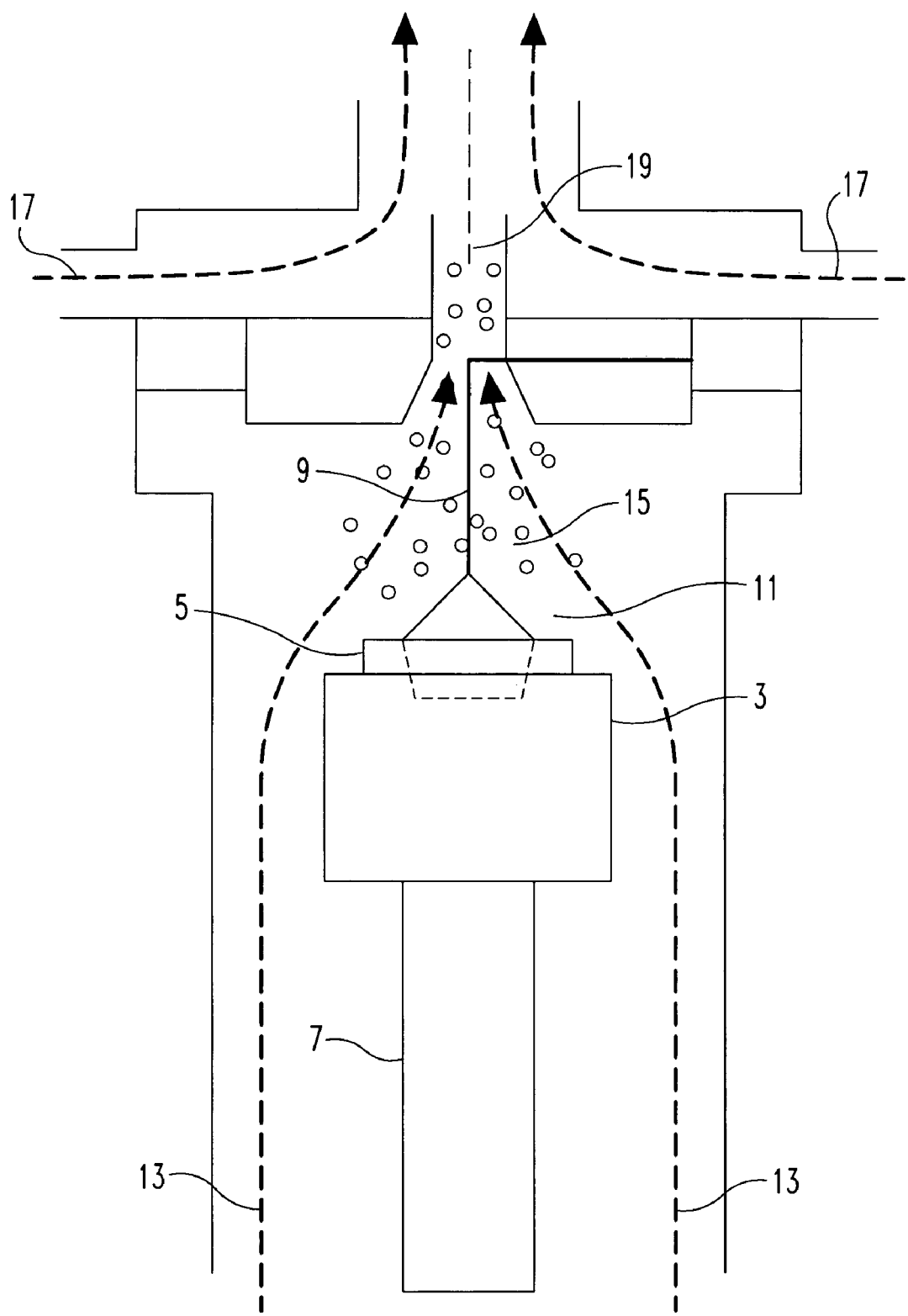
FIG. 1 is a schematic drawing of the arc region of a representative distributed arc cluster source (DACS) for use in synthesizing the nanoparticles of the invention.

FIG. 1 shows an embodiment of a distributed arc cluster source 1. Tungsten feed crucible 3 is surrounded by tantalum shield 5 and mounted on positive biased carbon rod 7 in proximity to tungsten electrode 9. A metal or metal mixture is placed in open tungsten crucible 3, and this metal charge is evaporated by means of an atmospheric pressure direct current (d.c.) arc discharge 11 established between the melt and the tungsten electrode 9. Carrier gas flow 13, room temperature argon, entrains the evaporating metal atoms 15 and rapidly cools and dilutes the metal vapor, causing solid particles to nucleate and grow. Particles 19 are produced as bare metal clusters entrained in the gas; the synthetic process leaves their surfaces free of organic molecules of any kind and ready for functionalization. Quench gas flow 17, room temperature helium or nitrogen, further cools the particles 19 and transports them to a vessel where they are contacted with a liquid and captured as a colloidal suspension (see FIG. 2) rather than being deposited on a substrate.

The mean size of the particles is a function of both the metal evaporation rate, which is controlled by the power to the arc, and the gas flow rates. Preferably, the nanoparticles have a mean diameter of about 5 nm to about 50 nm and a variance of less than 50% of the mean. Size-selective precipitation can be used to reduce the variance, e.g., to approximately 5% of the mean.

The mean composition of the particles (in the case of a mixed metal charge) depends on the relative evaporation rates of the components in the charge and is a function of the composition of the molten mixture in the crucible. In the present case this is a mixture of Fe and Au of known composition. A specific composition in the crucible yields a specific particle composition.

Figure 2:
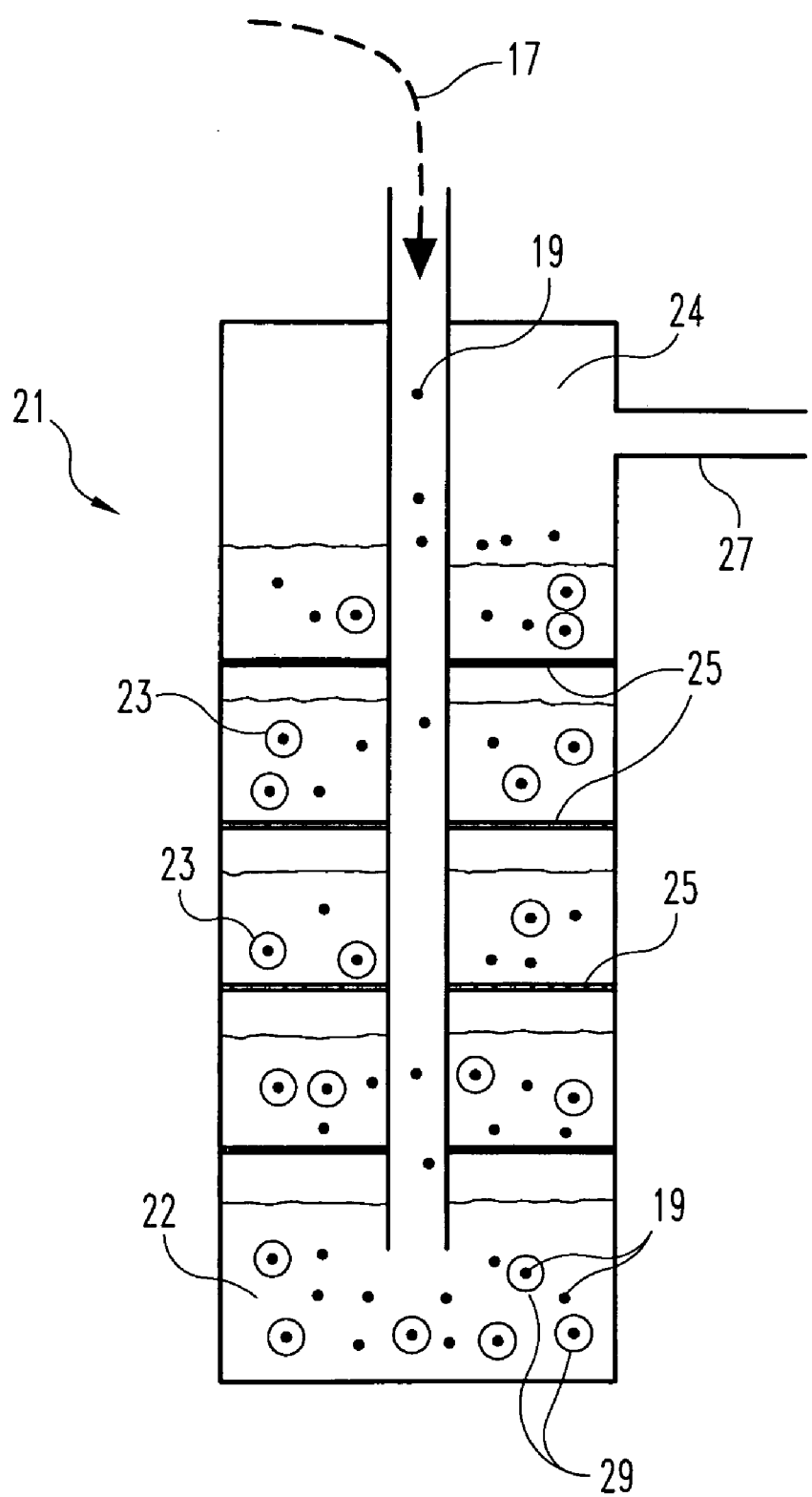
FIG. 2 is a schematic drawing of a representative capture cell for use in capturing the nanoparticles of the invention as a stable suspension.

FIG. 2 shows an embodiment of capture cell 21 used in the synthesis of the nanoparticles according to the invention. Capture cell 21 contains multiple liquid-filled vertical chambers 23 connected by baffle plates 25. Quench gas 17 carrying nanoparticles 19 from the distributed arc cluster source (FIG. 1) is injected into the liquid contained in capture cell 21. Nanoparticles 19 are captured in liquid in the bottom chamber 22 and percolate up through the liquid in successive vertical chambers 23. Gas bubbles rise 29 and contact baffle plates 25 as they enter the vertically adjacent chamber 23. As they rise in a liquid gas bubbles naturally coalesce, and gas may build up underneath the baffle plate 25. Perforated baffles break up the gas into smaller bubbles each time it passes through a baffle plate. This gives the particles 19 still entrained in the gas more opportunity to contact, and thereby transfer into, the liquid. Quench gas 17 exhausts from outlet 27 in the uppermost vertical chamber 24. The liquid in capture cell 21 is well mixed by the gas flow and no segregation of particles 19 in the different chambers as defined by baffle plates 25 is typically observed.

Figure 7:
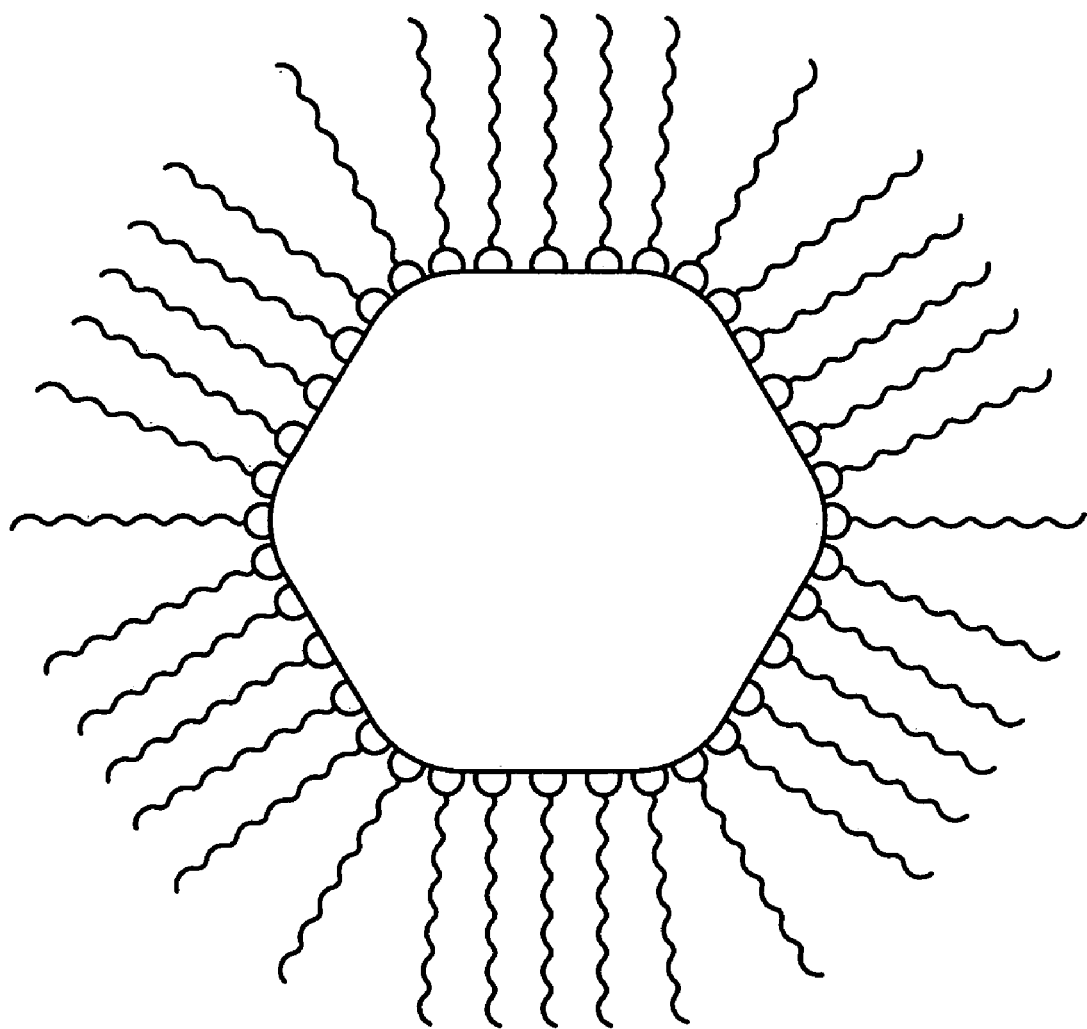
FIG. 7 is a schematic drawing of Fe/Au nanoparticle surrounded by a protective monolayer of linear organic molecules, e.g., a mixed monolayer of dodecanethiol and dodecylamine, which provide colloidal stability in organic solvents.

In one embodiment, nanoparticles 19 are captured in an organic solvent. When capturing particles in an organic solvent such as mesitylene, additional molecules that rapidly coat the particles with a covalently attached monolayer, such as dodecanethiol and dodecylamine (see FIG. 7) are preferably added to the solvent, for example at a concentration of about 1.0 mM. These organic additives attach directly to particles 19 and protect them from aggregating in capture cell 21.

In another embodiment, nanoparticles 19 are captured in an aqueous liquid such as a dilute sodium citrate solution to produce a charge-stabilized nanocolloid. The negative citrate ions form a diffuse layer around the metal nanoparticles and keep them in suspension without aggregation. This is also a convenient starting point for further functionalization reactions. Optionally, one or more organic molecules such dodecanethiol and dodecylamine can be added, typically with a cosolvent, such as ethanol, to the citrate stabilized suspension. When these organic molecules react with the Fe/Au particles in an aqueous environment, they cause the particles to flocculate and drop out of solution. The particles can then be dried and re-suspended in an organic solvent such as dichloromethane, and have been shown to be equivalent to particles captured directly in an organic solvent in which dodecanethiol and dodecylamine have been added.

In yet another embodiment, nanoparticles 19 are captured in an aqueous liquid such as a dilute sodium citrate solution that contains one or more functionalizing molecules, allowing capture of the charge-stabilized nanocolloid and functionalization to be performed in a single step rather than in successive step.

The resulting colloidal suspensions are stable for weeks and the particles can be stored in this state.

Diameter and Composition of the Fe/Au Nanoparticles

Figure 3:
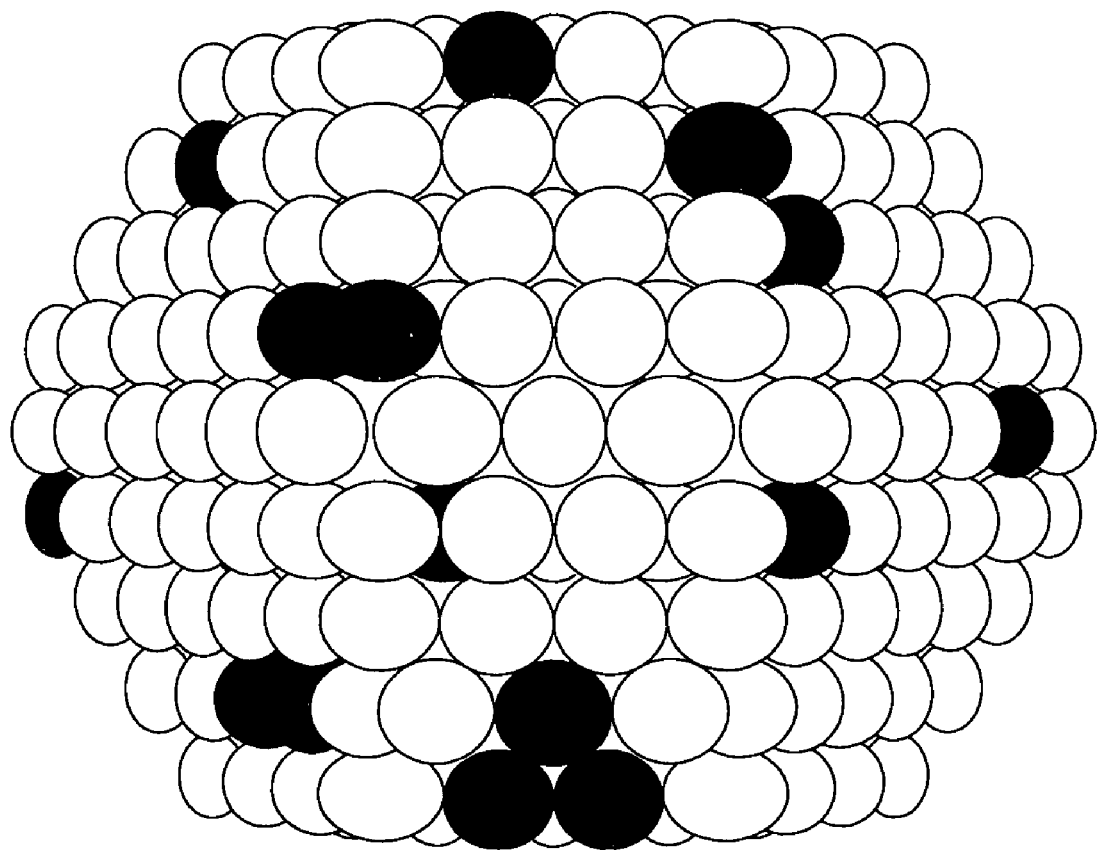
FIG. 3 is a schematic drawing indicating the random distribution of Fe atoms (dark spheres) and Au atoms (light spheres) on the surface of a 2.5 nm diameter Fe(10)/Au(90) nanoparticle.

The Fe/Au nanoparticles are defined herein by the diameter and composition of the Fe/Au nanoparticle or, in the case of a functionalized nanoparticle, the Fe/Au metal core. For example, "10 nm diameter Fe(60)/Au(40)" indicates a particle (or metal core) with a 10 nm diameter core having an atomic composition 60% Fe atoms and 40% Au atoms. In a preferred embodiment, the Fe atoms and the Au atoms are distributed randomly within the nanoparticle or nanoparticle core (FIG. 3).

Diameters of the nanoparticles of the invention are preferably at least about 5 nm and at most about 50 nm, although particles smaller (e.g., diameter of about 2.5 nm) or larger (e.g., diameter of about 100 nm) can be produced using the method described herein.

Figure 4:
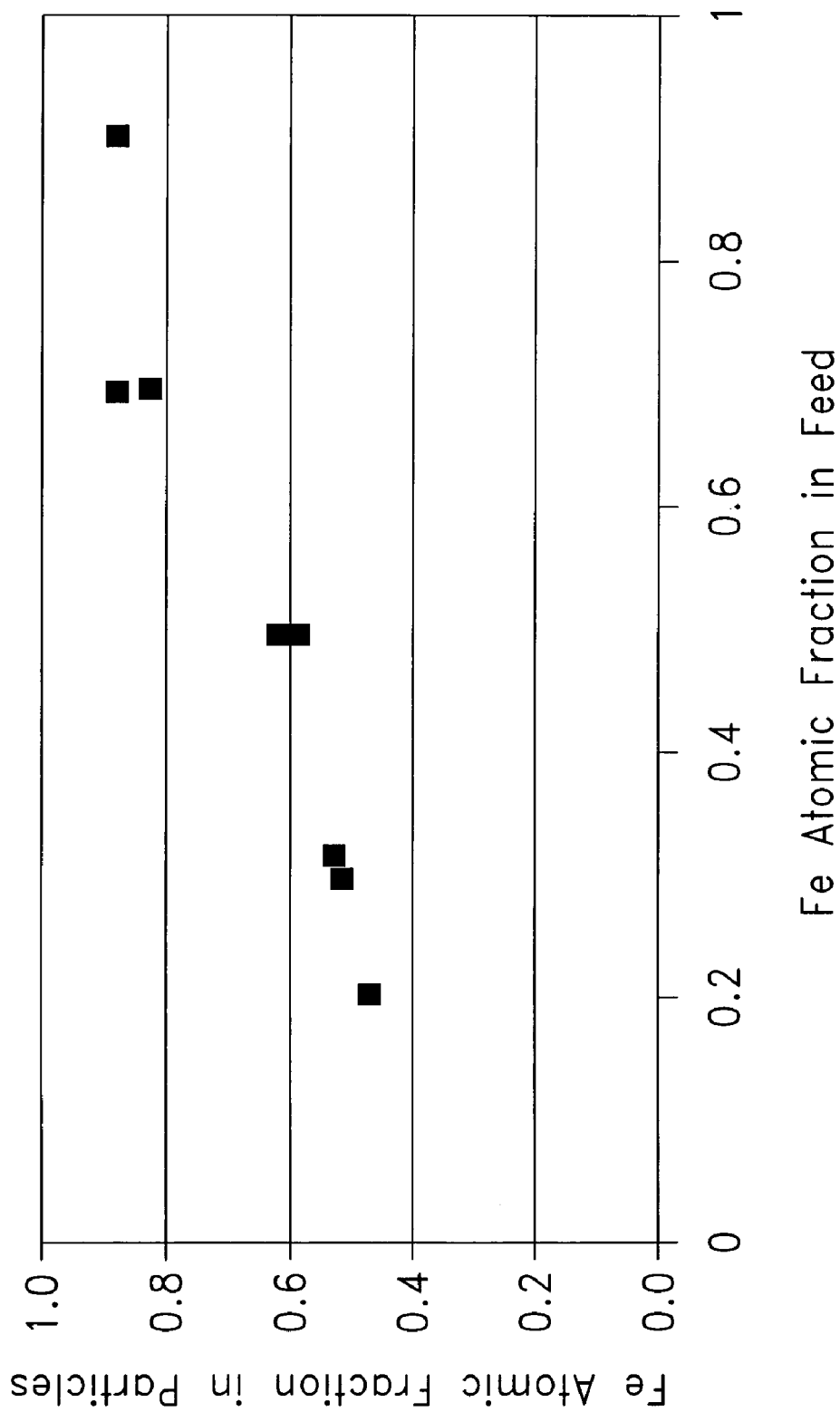
FIG. 4 shows the atomic fraction of Fe in nanoparticles produced in the DACS as a function of the atomic fraction of Fe in the crucible.

Atomic adsorption experiments made by dissolving a large number of identical Fe/Au particles in acid can used to determine their composition. Transmission electron microscope images made by supporting large numbers of the same Fe/Au particles on thin carbon membranes have shown that the particles have an essentially random distribution of Fe and Au atoms (i.e., the Fe and Au atoms do not segregate into observable Fe rich and Au rich regions or phases) as long as the Fe atom/Au atom ratio does not exceed about 7:3, i.e., Fe(70)/Au(30). Above 70 atomic % Fe however, phase segregation is observed. Particles with Fe atomic fractions of 50% or less were found to have reproducible magnetic characteristics and surface functionalization. FIG. 4 shows the Fe content of the particles as a function of the ratio of Fe to Au in the metal charge (feed).

The Fe content of the nanoparticles of the invention is preferably at least about 0.01%; (i.e. Fe(0.01)/Au(99.99)); more preferably it is at least about 5% (i.e., Fe(5)/Au(95)). At most, the Fe content of the nanoparticles is preferably about 70 atom % (i.e., Fe(70)/Au(30)); more preferably it is at most about 50% (i.e., Fe(50)/Au(50)).

Figure 5:
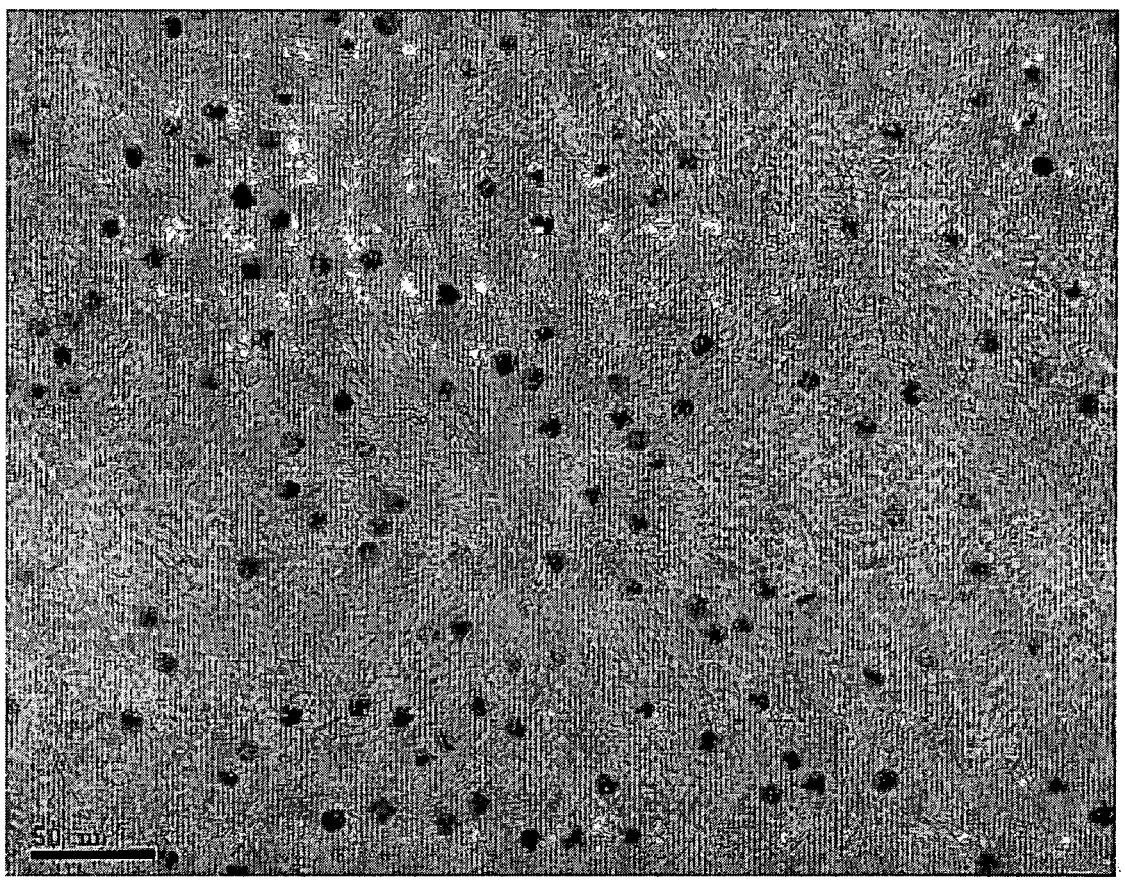
FIG. 5 is a transmission electron microscope (TEM) micrograph of 10 nm diameter Fe(50)/Au(50) nanoparticles produced using the distributed arc cluster source of FIG. 1.

FIG. 5 shows a TEM micrograph of a sample of uniform 10 nm diameter Fe(50)/Au(50) particles. The nanoparticles were captured as a stable colloid by bubbling the aerosol stream from the DACS into distilled water containing sodium citrate. The particles were then coated with a mixed monolayer of dodecanethiol and dodecylamine molecules by adding dodecanethiol and dodecylamine in ethanol to the colloidal solution. The coated particles precipitated spontaneously from the aqueous solution, were dried and re-suspended in dichloromethane. The careful addition of acetonitrile, which is a poor solvent for the particles, was used to narrow the particle size distribution by size-selective precipitation. The TEM sample was obtained by spreading a drop of the dichloromethane solution on a copper TEM grid coated with a thin carbon film.

The nanoparticle is thought to contain only zero valent iron and gold, however, some of the Fe atoms, especially those on or near the surface, may be oxidized.

Magnetization

The relationship between the field experienced within a sample and the applied field is known as the magnetic susceptibility. Magnetic susceptibility is calculated as the ratio of the internal field to the applied field and represents the slope of the curve of magnetization (M) vs. magnetic field strength (H). It is typically expressed as volume susceptibility (emu/Oe-cm$^3$, or simply, emu/cm$^3$), mass susceptibility (emu/Oe-g, or emu/g) or molar susceptibility (emu/Oe-mol, or emu/mol).

Figure 6A:
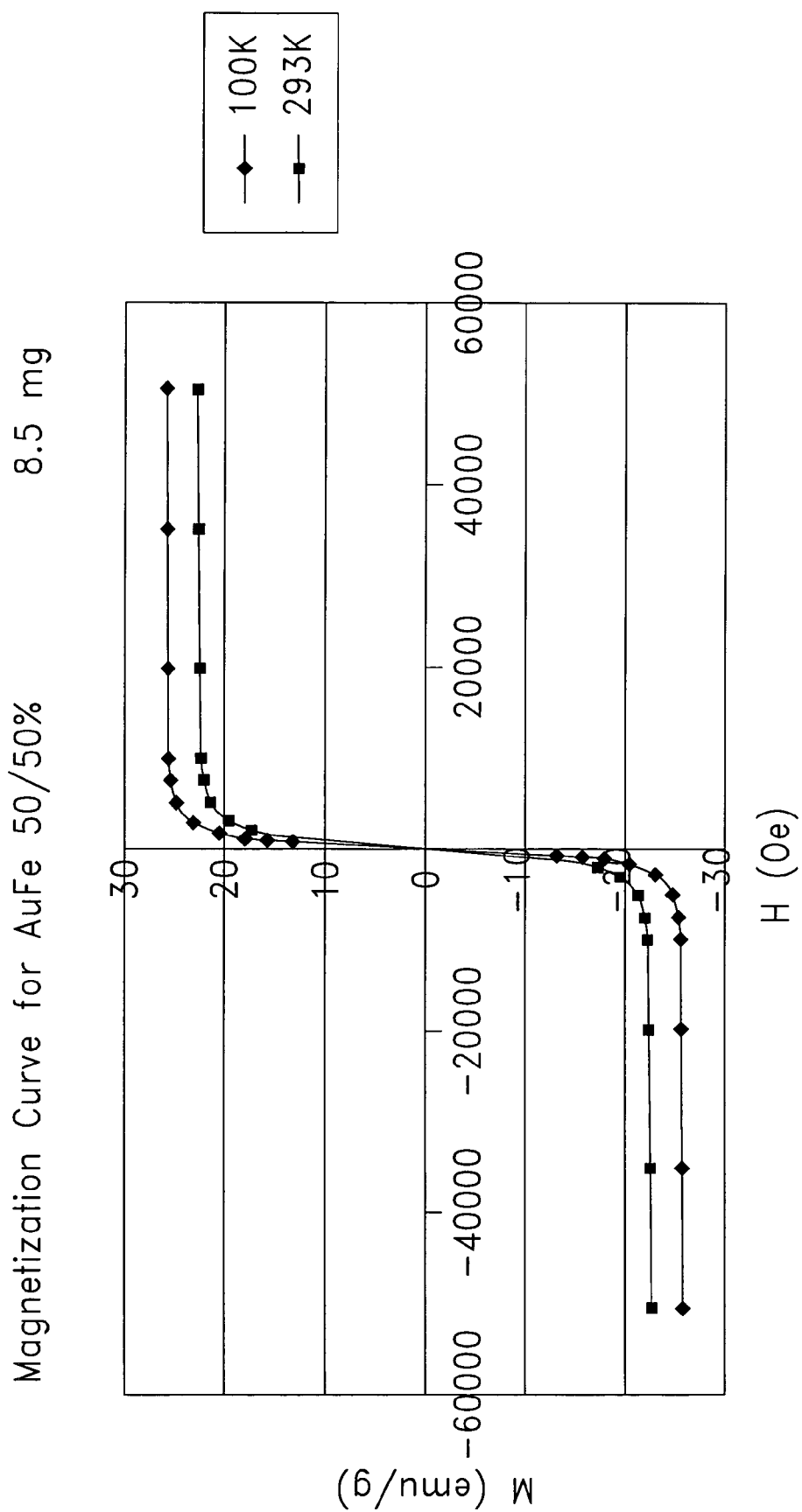
FIG. 6a is a graph showing a pair of magnetization curves (at 100K and 293K) of a bulk sample of Fe(50)/Au(50) particles over the range 0–60,000 Oe.
Figure 6B:
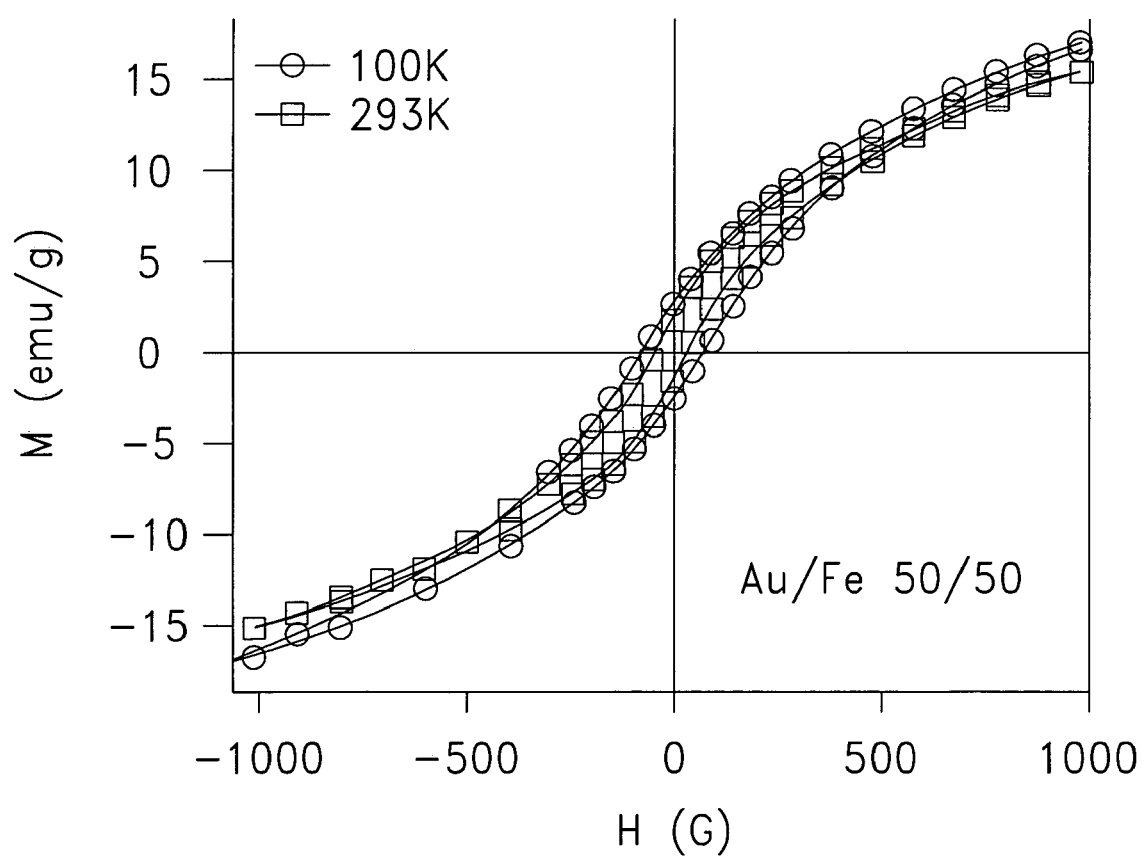
FIG. 6b is a graph showing a pair of magnetization curves (at 100K and 293K) of a bulk sample of Fe(50)/Au(50) particles over the range 0–1000 Oe.

The nanoparticles exhibit strong magnetic susceptibility and stable magnetic characteristics. The magnetic characteristics of Fe/Au particles can be measured by capturing a sample of particles of known weight and measuring the magnetization curve of the bulk sample. The results of a representative experiment for the particles shown in FIG. 5 are shown in FIG. 6. Fe/Au particles with an average diameter of 10 nm and an Fe composition of 50 atom % (Fe(50)/Au(50)) were coated with a mixed monolayer of dodecanethiol and dodecylaminemolecules and were magnetically collected from a mesitylene solution. They exhibited a saturation magnetization (attained when all magnetic moments in the sample are aligned) at 293K of 22.5 emu/g or 280 emu/cc (FIG. 6a). This is equivalent to a saturation magnetization of ~100 emu/g Fe. The magnetic susceptibility of these nanoparticles is 0.2 emu/Oe-cm$^3$ (emu/cm$^3$) over the range 0–1,000 Oe and 0.25 emu/Oe-cm$^3$ (emu/cm$^3$) over the range 0–500Oe (FIG. 6b). Prior art micron-scale nanoparticles have magnetic susceptibilities that are orders of magnitude less than the 0.1 to 0.2 emu/cm$^3$ at 293K that characterizes the nanoparticles of the invention. Furthermore, the nanoparticles of the invention are not susceptible to loss of their magnetic properties due to the chemical transformation of magnetic iron oxides to diamagnetic $Fe_2O_3$ as are the prior art particles.

In addition, because the diameter and Fe/Au ratio of the particles can be accurately controlled, the magnetic moments of the Fe/Au particles can also be controlled. Magnetization curves similar to those shown in FIG. 6 have been determined for samples of Fe/Au particles having different mean diameters and different compositions. These curves indicate that the Fe/Au nanoparticles are superparamagnetic with a saturation magnetic moment that, for a given mean diameter, is proportional to the Fe/Au ratio.

Surface Monolayers

The nanoparticles of the invention are initially produced as bare Fe/Au particles in a gas mixture of argon and nitrogen. It is frequently desirable to coat the particles with a monolayer of organic molecules to prevent nonspecific particle aggregation and/or to provide the functionality needed for an intended application. A wide range of organic molecules will react with the atoms on the surface of the Fe/Au particles to form a protective monolayer over the Fe/Au metal core. The preferred coating method depends on the structure of the organic molecule, its hydrophobic or hydrophilic nature, and whether the particles are captured in an aqueous or an organic solution. In a preferred embodiment, this is accomplished using thiol-terminated organic molecules so as to take advantage of the well-established reaction between thiol (—SH) and gold (Au).

When the organic molecules impart a hydrophilic nature to the surface of the particles, the particles are preferably first captured in a dilute aqueous solution of sodium citrate. This produces a charge-stabilized colloidal suspension that remains stable for many weeks. The organic molecules are subsequently added as a dilute solution to this colloidal suspension of charge-stabilized particles.

The attachment of organic molecules that impart a hydrophobic nature to the surface of the particles is preferably performed in either of two ways. When the organic ligand is water soluble or can be made soluble by the addition of a cosolvent such as ethanol, the particles are first captured in a dilute aqueous solution of sodium citrate as they are prior to functionalization with a hydrophilic ligand. The organic ligand is subsequently added to this colloidal suspension, optionally in the presence of a colsovent, to react with the particles. Adding a linear alkanethiol to the liquid, for example, and a cosolvent such as ethanol (to increase the solubility of a hydrophobic ligand such as an alkanethiol), causes the particles to be rapidly coated with a monolayer of the alkanethiol. The thiol groups react with gold atoms on the surface of the Fe/Au particles and encapsulate the particles with a hydrophobic monolayer. The elimination of charge on the particles and the encapsulation of the particles by a hydrophobic monolayer causes the nanoparticles to aggregate and settle out of solution.

Figure 8:
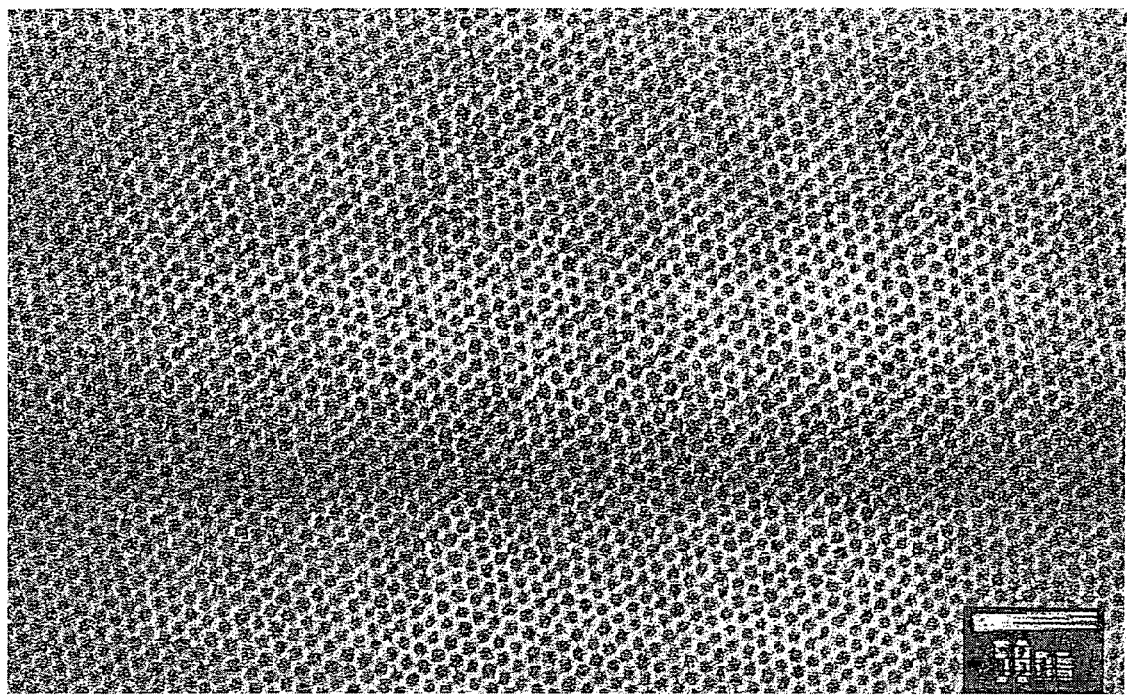
FIG. 8 is a TEM micrograph of an ordered monolayer of 5 nm diameter Fe(00)/Au(100) particles coated by a protective monolayer of dodecanethiol. The extremely small size spread exhibited by this sample is illustrative of the degree of control that can be achieved by size-selective precipitation.

Once the coated particles are washed and air-dried, they can be re-suspended in an organic solvent such as dichloromethane or mesitylene (1,3,5-trimethyl-benzene). When re-suspended in an organic solvent the particles can be manipulated as stable physical entities and/or the alkanethiol molecules can be displaced by other organic thiols or dithiols. The Fe/Au particles encapsulated by a hydrophobic monolayer such as provided by a linear alkanethiol can be self-assembled into ordered arrays (FIG. 8) and molecularly linked together by bifunctional molecules such as conjugated dithiols or di-isonitriles to form thin films and bulk materials with interesting electrical and magnetic properties (Andres et al., *Science* 273, 1690 (1996)).

The second way in which organic molecules that impart a hydrophobic nature to the surface of the particles can be attached to the bare particles is to capture the particles directly in an organic solvent such as mesitylene in which one or more hydrophobic molecules such as dodecanethiol and/or dodeylamine have been added (Andres et al., *Science* 273, 1690 (1996)). Because of the presence of Fe atoms as well as Au atoms on the surface of Fe/Au particles, it is found that a mixed monolayer such as is produced by including both a thiol such as dodecanethiol and an amine such as dodecylamine provides the best encapsulation. When the particles are coated with an alkanethiol or other hydrophobic organic ligand monolayer and are suspended in an organic solvent, it is possible to cause them to aggregate and precipitate by adding a poor solvent such as ethanol or acetonitrile to the solution. Once the particles are air-dried they can be re-suspended in clean solvent and manipulated as described in the previous paragraph.

In addition to the functionalization with alkanethiols, other functionalization reactions that can conveniently be performed on charge-stabilized nanoparticles include, but are not limited to, adding a thiol-terminated polyethylene glycol (PEG) molecule to coat the particle with a hydrophilic monolayer, adding a DNA oligomer that is terminated by an linear alkane spacer and a thiol ligand, adding thiolpyridine to functionalize the particles with pyridine, and adding bis (p-sulfonatophenyl) phenyl phosphine for producing uniformly charged particles that are ideal for size selective separation of the particles in aqueous solution.

Notwithstanding the above, it should be understood that the invention is not limited by the type of linkage between the organic molecule and the metal core. For example, the linkage can be chemical or enzymatic, and can be covalent, ionic, or hydrophobic in nature.

For many applications, especially biological and biomedical applications, it is important to produce Fe/Au nanoparticles that are water-soluble. That is, they must be functionalized so that they remain hydrophilic. For example, it may be desirable to functionalize the Fe/Au core with DNA. This can be been done by adding to the citrate solution DNA oligomers that are terminated by a linear methylene sequence, a disulfide group, a second linear methylene sequence and an OH group (Nature 382, 607 (1996)). These DNA oligomers encapsulate the Fe/Au particles and produce stable physical entities that can be precipitated from the aqueous solution by adding excess electrolyte. Decanting the liquid and adding fresh water re-suspends the particles. Functionalizing the particles in this way with single-stranded DNA provides a method by which the Fe/Au particles can be selectively linked to each other, to other DNA functionalized particles, or to solid surfaces to produce composite structures with interesting properties.

Other hydrophilic molecules besides DNA can be attached to the particles by means of thiol or disulfide groups. For example a polyethylene glycol (PEG) polymer terminated by linear methylene sequence terminated a thiol group can be added to the citrate solution to form a hydrophilic coating on the particles, pyridinethiol can be added to the citrate solution to coat the particles with pyridine ligands, and a great variety of biomolecules such as proteins, nucleic acids, carbohydrates, lipids, etc. can be similarly attached to the particles. Higher order biomaterials such an organelles, a membranes, cells or a complexes of cells can also be bound to the Fe/Au particles.

Fe/Au nanoparticles functionalized with specific biological binding moieties are expected to have many in vitro applications such as separation and detection of biomaterials. Because these nanoparticles are expected to be nontoxic and can move freely in the human circulatory system they also are expected to have multiple in vivo biomedical diagnostic and therapeutic applications.

Although the surface of the Fe/Au nanoparticles contains Fe atoms as well as Au atoms, many of the protocols developed to functionalize Au nanoparticles with specific biomolecules and bioreceptors may be used with the Fe/Au nanoparticles to produce functionalized Fe/Au nanoparticles that are water-soluble. Most of these protocols start with bare Au nanoparticles in a dilute aqueous sodium citrate solution, and they are equally applicable to bare Fe/Au nanoparticles. As an example of this approach, the protocol developed by Mirkin and his co-workers (Nature 382, 607 (1996)) which has been used by us to successfully functionalize Fe/Au nanoparticles with DNA oligomers.

The binding of biomaterials to the Fe/Au particles can also be accomplished by ionic forces using for example thiol-alkyl-sulfate or thiol-alkyl-amine molecules to impart a negative or positive charge on the particles or by specific antigen/antibody binding.

The ability to precipitate and then re-suspend particles protected by a tightly bound organic monolayer provides a way to narrow the particle size distribution by means of size-selective precipitation. For example, when the Fe/Au particles are coated with a monolayer of DNA oligomers, the first particles to precipitate as the electrolyte concentration is increased are the largest particles. Similarly, for particles coated with a monolayer of linear alkanethiol molecules, the first particles to precipitate as a poor organic solvent is added are the largest particles. Size-selective precipitation was used to prepare the monodispersed Fe/Au particle samples shown in FIGS. 4 and 7. For example, subjecting a population of nanoparticles having a mean diameter of about 5 mm to about 50 nm to size-selective precipitation can decrease the variance from about 50% of the mean to approximately 5% of the mean, significantly narrowing the size distribution of the particle population.

The present invention is illustrated by the following examples. It is to be understood that the particular examples, materials, amounts, and procedures are to be interpreted broadly in accordance with the scope and spirit of the invention as set forth herein.

EXAMPLES

Example I

Distributed Arc Cluster Source (DACS) Operating Conditions for Synthesis of Au—Fe Nanoparticles The total mass of metal placed in the DACS crucible was about 0.5 g with a known gold to iron weight ratio. The gold and iron used were 0.04 in diameter wires purchased from Alfa Aesar and were at least 99.9% pure. Argon was used as the inert gas in the arc chamber. The argon flow rate was 120 $cm^3/s$ at a pressure of 30 psig. Nitrogen or helium gas was used as the quench gas with a flow rate of 250 $cm^3/s$ or 425 $cm^3/s$, respectively, at a pressure of 40 psig. Argon was allowed to flow through the apparatus for about 20 minutes prior and after a run. The gold-iron mixture in the crucible was heated with the plasma arc for five to ten seconds at an input voltage of 75% to pre-melt the feed before starting a run. This was done to homogenize the charge in the crucible. About 2–20% of the feed was evaporated during this pre-melt step.

To initiate the arc plasma, the variac was set at 75%. At this setting, the initial voltage drop between the tungsten electrode and the crucible was about 50V. Once the arc plasma formed, this voltage drop decreased to 16–20V. The variac was then decreased to 55–62% for the remainder of the run. At this variac setting, the voltage drop across the arc ranged from 11V to 14.5V, depending on the condition of the charge, the crucible, and the tungsten electrode. For instance, if the crucible is old with metal residues from previous runs or if the tungsten electrode is coated with evaporated metal, the voltage drop is usually higher. The voltage drop also increases with increasing distance between the tip of the tungsten electrode and the surface of the liquid pool in the crucible. For all the Au—Fe DACS runs in the present application, this distance was always set to be approximately 5 mm.

During the DACS run, the arc voltage and the arc current stayed quite stable. This indicated the presence of a stable plasma throughout the run. The arc current typically ranged from 56A to 70A and the arc power, which was estimated by the product of voltage drop and arc current, ranged from 630W to 1040W. The metal evaporation rate ranged from 4 mg/hr to 350 mg/hr. The evaporation rate does not necessarily increase with increasing arc power as expected. Clearly, there are other factors that govern the condition of the DACS plasma and the evaporation rate. The expected correlation between arc power and evaporation rate is based on the assumption that the product of arc voltage and arc current is a good measure of the energy supplied to the melt and thus of the melt temperature. However, this may not be the case. A large fraction of the plasma power is dissipated by radiation, and the arc does not always center on the crucible. Furthermore, large variations in arc voltage were observed at the same arc current, and the arc voltage does not necessarily increase with increasing applied current. This seems to indicate that the arc voltage is more dependent on the conditions within the melt or the arc.

Temperature measurement experiments done by others on a pure argon arc with tungsten/copper electrodes have shown that the temperature profile of a plasma arc does not vary significantly with small changes in arc power, and the arc has a temperature gradient such that the temperature is highest at the center of the arc near the cathode and decreases towards the anode and the outer periphery of the arc. It is speculated that the variation in DACS evaporation rate may be due to variations in the distribution of the melt in the crucible, i.e. whether the melted metal in the crucible is gathered at the center of the crucible or plated on the sides of the crucible. Both conditions were observed when the apparatus was cooled down after the pre-melt. It is not clear what causes these variations. The variation in DACS evaporation rate may also be due to variation in the alignment of the tungsten electrode. Although it is assumed that the arc is distributed evenly between the tungsten electrode and the melt in the crucible, this may not always be the case. If the tungsten electrode is slightly askew, the plasma may be centered on one side of the crucible, resulting in the melt not being heated uniformly. At times, the tantalum shield surrounding the crucible melted on one side, indicating an electrode misalignment. Thus, slight misalignment of the tungsten electrode can affect the uniformity of the arc and thereby the evaporation rate.

In cases of especially high evaporation rate (above 100 mg/hr), the plasma arc was most often unstable at low input current and the stable arc voltage was usually high (above 13V). This is consistent with experimental characteristics found when an element with high ionization potential such as nitrogen, hydrogen or carbon is introduced into an argon arc. In such cases, the temperature of the arc is higher than that of a plasma arc sustained solely by ionized metals with much lower ionization potentials. During the pre-melt of the DACS feed, the arc at times sputtered some carbon from the graphite crucible holder and coated the metal feed and tungsten crucible with a thin layer of carbon. The presence of carbon in the arc might have caused an increase in arc temperature and thus increased the evaporation rate.

Table 1 summarizes the average evaporation rates and arc powers for various Au/Fe feed compositions. The arc power needed to sustain the arc does not show any distinct correlation with the feed composition, however, the evaporation rate is seen to generally increase with increasing gold composition. There also seems to be a step increase in evaporation rate between feed compositions below and above 50/50%. Perhaps this is because gold has a higher ionization potential than iron. In the presence of a gold-rich feed, the plasma arc is predominantly sustained by ionized gold vapor and would have a higher temperature than a plasma arc sustained by an ionized vapor containing more iron ions. This effect of gold can be especially seen in the 80/20% Au/Fe runs, which has consistent high arc voltages.

TABLE 1

Average evaporation rates and arc powers for various Au/Fe feed compositions.

| Molar Feed Ratio (Au/Fe %) | Average Evaporation Rate (mg/hr) | Average Evaporation Rate (mol/hr) | Average Power (W) |
|---|---|---|---|
| 10/90% | 37.5 | 5.15E−04 | 775.12 |
|  | 32.0 | 3.54E−04 | 841.07 |
| 50/50% | 76.1 | 6.68E−04 | 753.82 |
| 60/40% | 121.4 | 1.02E−03 | 760.26 |
| 70/30% | 132.2 | 1.06E−03 | 727.27 |
| 80/20% | 142.1 | 1.07E−03 | 811.62 |

Example II

Sample Preparation and Analytical Methods Used to Characterize Au—Fe Nanoparticles The average composition of a sample of Au—Fe nanoparticles was determined using a Perkin Elmer AAnalyst 300 Atomic Absorption (AA) Spectrometer. This instrument determines the analyte concentration by measuring the amount of light absorbed by the analyte ground state atoms. Since each element only absorbs light energy of a specific wavelength, each element has its own specific AA operating conditions. The gold concentration was determined using a gold hollow cathode lamp (Fisher Scientific) at a wavelength of 242.8 nm, a slit width of 0.7 nm, and an input current of 8 mA (80% of the rated maximum current). The iron concentration was determined using an iron hollow cathode lamp at a wavelength of 248.3 nm, a slit width of 0.2 nm, and an input current of 24 mA. For each analysis, the spectrometer was calibrated with two to three samples diluted from AA standard solutions (Alfa Aesar). The gold standards used for calibration and the sample gold concentration typically ranged from 0 to 20 ppm, which is within the operating linear range for gold (0–50 ppm). For iron, the standard and sample concentrations were kept within the linear range of 0–10 ppm. The AA flame used for both gold and iron analysis was a lean blue air-acetylene flame. The recorded AA concentration was an average of five replicated readings taken 1s apart.

The morphology, homogeneity, and size of the nanoparticles were examined using a JEOL 2000FX Transmission Electron Microscope (TEM). The operating electron energy was at 200 keV. The TEM micrographs were taken at a magnification of ×100–600k using a digital camera operated by the Gatan Digital Micrograph software. The TEM samples were prepared on carbon coated copper grids of 200 mesh purchased from Electron Microscopy Sciences. The size distribution of the nanoparticles was determined from the TEM micrographs using Optimas 6.1 software and Image Tool software.

Magnetic properties of the nanoparticles were determined at Carnegie Mellon University by Dorothy Farrell working in the laboratory of Professor Sarah Majetich. A Quantum Design MPMS SQUID Magnetometer was used. The magnetic measurements were taken at 100K and 293K.

Atomic Absorption Spectroscopy (AAS) Analysis

Nanoparticles captured with organic surfactants can be separated from the capture solution by mixing a polar organic solvent such as acetonitrile or ethanol with the non-polar capture solvent to reduce the steric repulsion between the surfactant encapsulated nanoparticles. The Au—Fe nanoparticles were separated from the mesitylene capture solution by mixing equal volumes of acetonitrile [$CH_3CN$] and the nanoparticle solution. After about an hour, the mixture was centrifuged for 60 minutes to segregate out the nanoparticles, which deposited as black or brown solids at the bottom of the centrifuge tube. The precipitated Au—Fe nanoparticles were then dissolved in 1.0 ml of aqua regia diluted with 30 ml of deionized water. (Aqua regia was prepared by mixing 3 parts by volume of hydrochloric acid with 1 part nitric acid. All acids were obtained from Mallinckrodt and were at industrial strength.) However, acetonitrile also caused precipitation of some of the surfactant not absorbed on the nanoparticles. The precipitated surfactant that did not dissolve in the acid was filtered from the solution or removed by centrifugation. The filtration method was found to be a more efficient way of removing the surfactants and yielded more accurate results than the centrifugation method. The AA sample solutions have to be solid-free to prevent clogging of the spectrometer tubing. The acid content within the AA sample preferably does not exceed 5% by volume, which is the recommended maximum acid tolerance for the AA spectrometer.

Composition of Au—Fe nanoparticles used for magnetic measurements was determined by separating the nanoparticles from the capture solution with a permanent magnet (see later discussion) and dissolving a small amount of the dried nanoparticles in 1 ml of aqua regia diluted with 30 ml of deionized water. Magnetic separation of the particles managed to separate the nanoparticles from excess surfactant. Therefore, these samples did not have problems with undissolved surfactant, allowing cleaner dissolution of the particles as compared to the samples prepared by the acetonitrile precipitation method.

Au—Fe nanoparticles captured in water were simply dissolved by adding 1.0 ml of the nanoparticle solution to 1.0 ml of aqua regia diluted with 30 ml of deionized water.

Transmission Electron Microscopy (TEM) Analysis

TEM samples of organic solution captured nanoparticles can be prepared by casting a drop of the nanoparticle solution onto a TEM grid and slowly evaporating the solvent (Method 1). However, solvent evaporation does not remove excess surfactant from the TEM grid, as the surfactants are not volatile. Excess surfactants on the grid cause poor particle resolution and can oxidize or pyrolize in the electron microscope and hinder imaging. For accurate TEM imaging, the organic captured Au—Fe nanoparticles often had to be separated from the capture solution to remove excess surfactant. This was done by adding acetonitrile to the particle solution to precipitate the nanoparticles as described earlier. The precipitated nanoparticles were re-suspended in 1 ml of dichloromethane under ultrasonication.

Dichoromethane was used as opposed to mesitylene because it is much more volatile than mesitylene and facilitates the TEM sample preparation. The Au—Fe nanoparticles in dichloromethane were spread over a water surface framed with hexane. The hexane ring generally prevents the dichloromethane from sinking into the water phase as it has a higher density than water. The dichloromethane was allowed to evaporate and leave an array of nanoparticles on the water surface. The nanoparticle array was then transferred to a TEM grid by lightly touching the carbon coated copper grid on the water surface (Method 2).

TEM samples of Au—Fe nanoparticles in aqueous solution can be prepared by placing a drop of the particle solution onto the TEM grid and letting it dry in air (Method 3). This method, however, often results in the nanoparticles aggregating together as the water evaporates from the grid. Therefore, other methods were investigated to improve the quality of the sample. One of the methods used was mixing 100 μL of particle solution with 100 μL of tetrahydrofuran [$C_4H_8O$], placing the drop on a piece of Teflon, and heating it with a heat lamp (Method 4). As the drop evaporated, the nanoparticles were brought to the drop surface and formed a monolayer of particles on the surface. The nanoparticles were transferred onto the TEM copper grid by touching the grid on the drop surface. Another method was to cast a drop of the particle solution onto a TEM grid placed on a permanent magnet (Method 5). As the nanoparticles are magnetic, their magnetic moment causes them to be attracted to the magnet and to form chains of particles instead of dense aggregates. TEM analysis, however, showed that nanoparticle samples prepared by Method 4 and 5 do not significantly improve the dispersion or reduce the aggregation of the nanoparticles on the TEM grid as compared to samples prepared by Method 3.

Squid Magnetic Measurement

Au—Fe nanoparticles in organic solution were flowed slowly through a straw placed between the poles of a permanent magnet. The magnetic Au—Fe nanoparticles were deposited on the walls of the straw where the magnet was located. Nanoparticles that were extremely small or that had low magnetic moment bypassed the magnet and were captured in a flask. The nanoparticles deposited in the straw were dried on a petri dish and embedded in epoxy before being inserted into a clean straw for magnetic measurements.

The Au—Fe nanoparticles captured in water solution were first transferred into organic solution before being captured in the straw as described above. To transfer the charged stabilized nanoparticles into organic solution, 30 ml of the aqueous solution containing Au—Fe nanoparticles was added to 20 ml of ethanol and stirred for 2 minutes. A surfactant solution of 0.05M dodecanethiol, 0.02M didecylamine, and 0.03M dodecylamine in ethanol was prepared. 2 ml of the surfactant solution was added to the particle solution, and the mixture was stirred for 20 minutes. The nanoparticles encapsulated by the organic surfactants were separated from the solution by centrifugation and re-suspended in mesitylene under ultrasonication.

Example III

Stabilization of DACS Au—Fe Nanoparticles in Organic and Aqueous Solutions

This example describes experiments using different stabilizing agents to encapsulate Au—Fe nanoparticles in organic and aqueous solutions. Mesitylene (1,3,5-trimethylbezene), a non-polar solvent, was used as the organic solvent. The mesitylene used was purchased from Aldrich and had 97% purity. In mesitylene, oleic acid [$CH_3(CH_2)_7CH=CH(CH_2)_7CO_2H$], 1-dodecanethiol [$C_{12}H_{25}SH$], dodecylamine [$C_{12}H_{25}NH_2$], and didecylamine [$(C_{10}H_{21})_2NH$] were used as stabilizing surfactants. The organic surfactants were purchased from Aldrich and had 98% purity. Oleic acid was used by itself and was prepared by adding 0.282 g (1 mmol) of oleic acid into 120 ml of mesitylene. The thiol and amine surfactants were used both by themselves and as mixtures in mesitylene. The usual amounts of dodecanethiol, dodecylamine, and didecylamine used were 1.0 ml (4.2 mmol), 0.05 g (0.27 mmol), and 0.05 g (0.17 mmol), respectively in 120 ml of mesitylene.

Citric Acid [$HOC(CO_2H)(CH_2CO_2H)_2$], sodium citrate [$HOC(CO_2^-Na^+)(CH_2CO_2^-Na^+)_2$], Bis(p-sulfonatophenyl) phenyl phosphine dipotassium salt [$C_6H_5P(C_6H_4SO_3^-K^+)_2$], and methoxy polyethylene glycol-sulfhydryl [$CH_3—(OCH_2CH_2)_n—SH$] were used to stabilize the Au—Fe nanoparticles in water. These chemicals were purchased from Aldrich, Mallinckrodt, Strem Chemical, and SunBio PEG-Shop, respectively, and had 99% purity. The usual amounts used were 0.31 g (1.61 mmol) for citric acid, 0.04 g (0.17 mmol) for sodium citrate, 0.1 g (0.2 mmol) for phenyl phosphine, and 1.16 g (0.58 mmol) for polyethylene glycol in 120 ml of water.

Au—Fe Nanoparticles Captured with Oleic Acid in Mesitylene

The first organic surfactant used to capture the Au—Fe nanoparticles in organic solution was oleic acid. Oleic acid was chosen to capture the Au—Fe nanoparticles because it has been known to successfully stabilize silver particles in organic solution, and the surface properties of silver is quite similar to gold. The long carbon chain of oleic acid makes it soluble in organic solvents, while its polar carboxylic acid end attaches to the surface of the Au—Fe nanoparticles. The Au—Fe nanoparticles formed a metastable colloid in oleic/mesitylene solution and had a faint pinkish color. From TEM micrographs of 50/50% Au/Fe feed ratio nanoparticles captured with oleic acid in mesitylene, the particles appear to have an average size of 10 nm. It is also apparent that excess oleic acid remains on the TEM grid once the mesitylene evaporated.

Oleic acid captured nanoparticles could not be easily re-suspended in organic solvent once they had been centrifuged from a mixture of capture solution and acetonitrile. This is believed to be due to the fact that the oleic acid molecule is not strongly bonded to the metal particles and can be easily displaced. The problems encountered with oleic acid led to trials of other organic surfactants to capture Au—Fe nanoparticles.

Au—Fe Nanoparticles Captured with Thiol Surfactant in Mesitylene

A DACS run with a 50/50% Au/Fe feed composition was performed with a dodecanethiol/mesitylene capture solution. Dodecanethiol is known to bind strongly to gold surfaces, and thus was chosen to stabilize the Au—Fe nanoparticles. The Au—Fe nanoparticles suspended as metastable particles in thiol/mesitylene and formed a brownish solution. TEM micrographs were made of the Au—Fe nanoparticles captured with dodecanethiol surfactant in mesitylene. The nanoparticles are not uniform in size. The big nanoparticles might have formed during the DACS startup when the evaporation rate is higher. Big nanoparticles may also form in the gas phase or in the capture solution due to particle aggregation and flocculation before they can be encapsulated by the surfactants. On average, the thiol-encapsulated nanoparticles initially had an approximate size of 6 nm. However, the nanoparticles appeared to be unstable and grew in size after a couple of days in the capture solution. After about 20 days, the particles have grown to about an average size of 10 nm. This particle growth may due to the weak bonding of the alkanethiol on surface iron atoms. This results in the formation of a defective SAM layer or partial coverage of the nanoparticles by the surfactant. Defects in the SAM layer coating the particles provide sites for particle growth or aggregation.

Au—Fe Nanoparticles Captured with Amine Surfactants in Mesitylene

A DACS run with 50/50% Au/Fe feed was performed with a mixture of dodecylamine and didecylamine surfactants in mesitylene. The amine surfactants were used because alkyl amines are known to bind on iron surfaces. The amines are expected to only bind weakly on gold surfaces. The Au—Fe nanoparticles suspended as metastable particles in the amine/mesitylene solution and formed a brownish solution. The Au—Fe nanoparticles captured with amine surfactants have an average size of 13 nm and are highly uniform in size compared to the dodecanethiol-captured nanoparticles. However, these amine-captured nanoparticles tend to flocculate and form nanoparticle aggregates.

Au—Fe Nanoparticles Captured with a Mixture of Thiol and Amine Surfactants in Mesitylene The Au—Fe nanoparticles from a DACS run with 50/50% Au/Fe feed composition captured with a mixture of dodecanethiol, dodecylamine, and didecylamine surfactants in mesitylene formed a brownish solution. The mixed surfactant captured Au—Fe nanoparticles have a fairly wide size distribution, which typically ranges from 5 to 50 nm. The average particle size is estimated to be 10 nm. These nanoparticles are much more stable than the nanoparticles captured with either thiol or amine surfactants alone. The presence of acetonitrile tends to reduce the steric repulsion and causes the particles to flocculate. However, the Au—Fe nanoparticles do not appear to have aggregated or grown in size. The average particle size is still 10 nm. The stability of these nanoparticles is thought to be due to the effective coverage of the nanoparticles with surfactants that have great affinity towards both gold and iron surface atoms. The amine surfactants are expected to bind strongly to the iron surface atoms and the thiol surfactant to the gold surface atoms.

Of the organic solutions examined, the mixed surfactant solution with both thiol and amine surfactants was found to be the most effective capture solution for the DACS synthesized Au—Fe nanoparticles. The Au—Fe nanoparticles appeared to be most stable in this solution and could be easily resuspended in clean (surfactant-free) organic solution even after being centrifuged from the original capture solution. This mixed surfactant solution was therefore used to capture all the Au—Fe nanoparticles samples sent for magnetic analysis of the organic captured DACS nanoparticles.

Au—Fe Nanoparticles Stabilized with Citric Acid in Water

Citric acid was first used as a water-soluble capture agent because citrate ion is used as the stabilizing agent for commercially available Au colloids. Au—Fe nanoparticles captured using citric acid formed a slightly pink solution and were very uniform in size. The Au—Fe nanoparticles from a 50/50% Au/Fe feed composition DACS run captured in a citric acid/water solution have an average size of 10 nm. However, after one day in the solution, most of the particles settled out of the solution and the capture solution became greenish in color. It is suspected that the iron atoms were leached from the particles and formed Fe(III), which is green in color when dissolved in water. AA analysis on the aqueous solution of nanoparticles captured using citric acid yielded a constant iron composition of 99% regardless of the variation in the DACS feed iron composition from 40–70%. It is felt that the nanoparticles had largely precipitated, leaving a solution containing mainly of dissolved iron. To test this hypothesis, the precipitated particles of a 30/70% Au/Fe DACS sample were analyzed by AA and were found to have a composition of 23% Au and 77% Fe while the composition obtained for the bulk solution containing the suspended "particles" was 1% Au and 99% Fe. In a second experiment, Au—Fe nanoparticles from a 50/50% Au/Fe DACS run that were sampled by dissolving the particles that had deposited on the plastic tubing leading from the DACS to the capture vessel were found to have a composition of 41% Au and 59% Fe while the composition of the citric acid "colloidal" solution from the same run had a composition of 10% Au and 90% Fe. Thus, citric acid is not an effective capture agent for Au—Fe nanoparticles in water.

Au—Fe Nanoparticles Stabilized with Bis(p-Sulfonatophenyl) Phenyl Phosphine Dipotassium Salt in Water This phosphine compound is known to stabilize Au particles in water. The phenyl groups attached to the phosphorous atom are functionalized with sulfates, which are negatively charged, and impart charge stabilization to Au nanoparticles.

The Au—Fe nanoparticles suspended in the phosphine/water capture solution and formed a brownish solution. The Au—Fe nanoparticles captured with phosphine in water from a 50/50% Au/Fe feed composition DACS run have a size range of 3–25 nm and an average particle size of 8 nm.

Au—Fe Nanoparticles Stabilized with Sodium Citrate in Water

The citrate ion has three carboxylic groups, which become negatively charged when dissolved in water. The citrate ions will therefore be drawn towards positively charged metal particles in water and form an electrical double layer around the particles. Citrate is known to stabilize Au particles in water.

The Au—Fe nanoparticles suspended in citrate/water capture solution and formed a brownish solution. The Au—Fe nanoparticles from a 50/50% Au/Fe DACS run stabilized by citrate in water had a size range of 3–20 nm and an average particle size of 6 nm.

Au—Fe Nanoparticles Stabilized with Methoxy Polyethylene Glycol Sulfhydryl (PEG—SH) in Water For many biological applications, it is desirable to produce Au—Fe nanoparticles that are stabilized by a water-soluble molecule that is covalently bonded to the particles. PEG—SH is a molecule with a thiol head group, which has great affinity towards gold atoms, and an ethylene glycol chain, which makes it soluble in water. Au—Fe nanoparticles captured using PEG—SH in water formed a brownish solution. The Au—Fe nanoparticles of a 50/50% Au/Fe DACS run captured by the PEG—SH in water have diameters ranging from 5 to 50 nm with an average size of 16 nm. The PEG—SH captured nanoparticles have an average size larger than those captured with either organic surfactants or phosphine and citrate ions. There is a likelihood that the PEG—SH is not able to attach to the particles quick enough to prevent particle aggregation in solution. In addition, the PEG—SH did not generally impart long-term stability to the nanoparticles. After two days, the solution lost its brown color and a large amount of yellow precipitate was found. TEM analysis of a sample of the solution revealed no observable particles. The yellow precipitates were checked for magnetism with a permanent magnet and were found to be not magnetic. It is believed that these precipitates largely consist of polymerized PEG—SH. It appears that the PEG—SH molecule is not able to efficiently capture and stabilize the Au—Fe nanoparticles in water.

Phase Transfer of Au—Fe Nanoparticles from an Aqueous Solution to an Organic Solution The Au—Fe nanoparticles captured in water were transferred into organic solution for preparation of magnetic measurement samples. This is to ensure that the nanoparticles do not aggregate and grow when they are separated out from solution by the magnet and dried prior to encapsulation in epoxy. Water-soluble stabilizing agents such as sodium citrate, which stabilize the particles by charge, lose their ability to prevent particle aggregation once the particles are not in solution. On the other hand, organic surfactants such as alkyl thiol and alkyl amine, which stabilize the particles by steric repulsion, form a SAM layer that is bonded to the particle surface and can thus prevent particle aggregation when the particles are not in solution. Phosphine stabilized and citrate stabilized nanoparticles were encapsulated by a mixture of thiol and amine surfactants with the procedure herein and examined for any changes in their physical properties.

Phosphine stabilized Au—Fe nanoparticles can be encapsulated with organic surfactants without any significant change in particle size. The Au—Fe nanoparticles (50/50% Au/Fe DACS feed) did not grow in size after being encapsulated by thiol and amine surfactants. The average particle size was 7 nm before and after the transfer. AA analysis of the particle composition before and after the transfer also showed that the particle composition did not change significantly. The average particle composition in phosphine solution was 45% Au and 55% Fe while the average particle composition in organic solution was 46% Au and 54% Fe. Therefore, phase transfer of phosphine stabilized Au—Fe nanoparticles into organic solution does not significantly change the size distribution or average composition of the nanoparticles.

The citrate stabilized Au—Fe nanoparticles can also be encapsulated with organic surfactants without significant changes in size or composition. Evaluation of the size distributions before and after encapsulating citrate stabilized Au—Fe nanoparticles with mixed thiol and amine surfactants showed that the nanoparticles retained their average particle diameter of 6 nm after the transfer. AA analysis on these Au—Fe nanoparticles showed that the average particle composition in the citrate solution was 46% Au and 54% Fe, and the average particle composition in the organic solution was 44% Au and 56% Fe. This slight difference in the particle composition may be due to the difficulty in determining an accurate gold composition in the particles captured using thiol surfactant. Thus, the particle properties are assumed to be unchanged during the process of transferring the citrate stabilized particles into organic solution.

Narrowing the Size Distribution of Au—Fe Nanoparticles

DACS synthesized Au—Fe nanoparticles captured in organic solution using mixed thiol and amine surfactants usually have a fairly wide size distribution. To improve the uniformity of the particle size, the Au—Fe nanoparticles stabilized by mixed thiol/amine surfactants can be selectively precipitated using acetonitrile. By adding a small amount of acetonitrile to the particle sample, the larger nanoparticles can be induced to flocculate and can then be removed from the solution by centrifugation while the smaller nanoparticles remain in solution. To size select the Au—Fe nanoparticles, a DACS nanoparticle sample was allowed to sit for a day to allow the largest nanoparticles to settle out of the capture solution. To a 4.8 ml sample of the colloidal suspension was added 1.2 ml of acetonitrile (20 volume %). The mixture was allowed to sit for 90 minutes before centrifuging it for 60 minutes. The precipitated particles, which looked black, were discarded, and to the remaining solution, which contained unprecipitated particles, was added with an additional 3.6 ml of acetonitrile (50 volume %). The mixture was allowed to sit for one hour before centrifuging it for another hour. The precipitated nanoparticles, which looked like a light brown solid, were allowed to dry. These dried nanoparticles were then resuspended in 1 ml of dichloromethane under ultrasonication to yield a brown suspension. The nanoparticles have a size range of 4 to 30 nm and an average size of 10 nm before size separation, and a tighter size range of 4 to 10 nm and an average size of 5 nm after size separation. Thus, the size distribution of the Au—Fe nanoparticles captured using the mixed thiol/amine surfactants can be improved by selective precipitation.

Citrate stabilized Au—Fe nanoparticles can be encapsulated with the mixed thiol/amine surfactants and transferred into mesitylene before being size selected by acetonitrile precipitation. The citrate stabilized Au—Fe nanoparticles were recaptured in organic with the procedure described herein, and size selected with the same procedure described above. However, in this case, the nanoparticles recaptured in organic solution from a citrate/water solution were size selected using 5 volume % acetonitrile instead of 20%. Before size selection, the nanoparticles had a size range of 3–12 nm and an average size of 6 nm. After size selection, the nanoparticles were very uniform in size with an average particle size of 5 nm. A direct procedure has yet to be found to successfully improve the size distribution of Au—Fe nanoparticles in aqueous solution without first transferring the particles into organic solution.

Example IV

TEM Analysis of the Structure of Au—Fe Nanoparticles

The DACS synthesized Au—Fe nanoparticles with feed compositions ranging between 30/70% and 80/20% Au/Fe were found by TEM analysis to exhibit no obvious segregation of the iron and gold atoms. It was found that the Au—Fe nanoparticles usually exhibit an even intensity across the particle image, implying that the particle density is uniform and that there is a uniform distribution of gold and iron atoms within the particles. The bigger particles are darker than the smaller particles due to the difference in electron scattering from particles of different thickness. However, particles of similar size also exhibit different intensities. This may be due to an uneven distribution of gold and iron among the particles or it may be due to difference in the orientation of these particles relative to the electron beam. Since gold has a higher atomic number than iron, it has a larger cross-section electron scattering than does iron, thus particles that are richer in gold are expected to look darker than the particles richer in iron. A few of the Au—Fe nanoparticles have different intensities within the particle itself, such as a dark ring surrounding a lighter core or a dark hemisphere attached to a lighter hemisphere. This is most probably due to formation of gold-rich and iron-rich phases within the particles.

For nanoparticles synthesized with feed composition above 70% Fe, a core-shell heterogeneous structure is observed. Since gold has a higher surface free energy than iron, most of the particles from a 10/90% Au/Fe feed run captured in citrate/water solution have a core-shell structure with a lighter iron-rich layer surrounding a darker gold-rich core. AA analysis of these heterogeneous particles showed that the particles have a composition of 12% Au and 88% Fe. Formation of core-shell heterogeneous particles is expected for Au/Fe compositions above 30/70% based on the Fe/Au binary phase diagram. Above this composition limit, an iron-rich phase is expected to precipitate first from a homogeneous liquid phase as the particle cools. Further cooling leads to formation of the gold-rich phase.

In conclusion, the TEM analysis indicates that DACS synthesized Au—Fe nanoparticles are single phase, i.e. homogeneous as long as the iron composition is less than ~70% although they are not necessarily uniform in size or composition.

Example V

Correlation Between the Composition of DACS Synthesized Particles and the Composition of the DACS Feed The composition of DACS particles was investigated to examine how the particle composition varies with the composition of the DACS feed. By manipulating the Au/Fe ratio, the magnetic moment of the Au—Fe nanoparticles can be controlled independently of particle size.

The evaporation in the DACS occurs at a very high temperature. Therefore, it is speculated that the partial pressures of Au and Fe vapor in the arc can be modeled using Raoult's Law, which states that the partial pressure of a component in an ideal system is equal to the product of its liquid phase composition and its pure vapor pressure. As the pure vapor pressures of Au and Fe are almost identical at high temperatures ($VP_{Fe}/VP_{Au}$=0.95 at ~3500K), it is expected that the evaporation rates of Au and Fe in the DACS should be approximately proportional to their relative compositions in the melt.

It can be seen from an analysis of gold atomic fraction in the DACS nanoparticles relative to the gold atomic fraction in the feed that the particle composition generally tracks the feed composition. However, there is a lot of scatter in the data. In particular, the composition of nanoparticles captured in organic solution does not appear to correlate well with the feed composition. For example, when the DACS feed composition is 50/50% Au/Fe, the average composition of the particles captured using the thiol surfactant alone is 33% Au and 67% Fe. However, with the same DACS feed, the composition of particles captured using the amine surfactant alone is 45% Au and 55% Fe. When the Au—Fe nanoparticles are separated from solution by adding acetonitrile and centrifuging, much of the excess surfactant also precipitates with the particles. As a result, when aqua regia is added to dissolve the clusters, white undissolved solids appear in the acid solution. The undissolved solids were removed by centrifuging or filtering the solution. However, the presence of excess surfactant appears to affect the analysis of the particle composition.

To investigate whether the thiol surfactant can remove gold from an acidic solution, an experiment was performed in which a small amount of dodecanethiol was added to a dilute solution of known gold concentration. When the dodecanethiol was added to the gold solution, it formed an immiscible layer on top of the aqueous solution. After a few hours, this dodecanethiol layer turned slightly red while the aqueous phase turned from bright yellow to light yellow. When aqua regia was added to the two-phase mixture, white solids appeared and the organic layer was no longer present. The white solids were removed from the solution by centrifugation, and the aqueous phase was checked for its gold concentration. AA analysis of the aqueous phase showed that the gold concentration was reduced by 55%. Therefore, the presence of excess dodecanethiol when the nanoparticles are dissolved in aqua regia prevents accurate analysis of the composition of the nanoparticles.

In order to test whether the amine surfactant also interferes with the composition analysis, a small amount of the mixed amine surfactant was added to a known mixture of iron and gold standard solutions containing aqua regia. The mixture was allowed to sit for a few days after which the amine surfactants were removed from the aqueous phase. The aqueous phase was analyzed by AA, and in this case, the gold and iron concentrations were found to decrease by only 6%, which could be due to experimental error. Therefore, the presence of amine surfactant probably does not interfere with the dissolution of Au—Fe particles in aqua regia.

It is speculated that the surfactant interference problem can be solved by filtering the undissolved solids from the acidic solution and then rinsing them thoroughly with deionized water to remove any retained metal atoms, or by repetitive precipitation and resuspension of the nanoparticles in fresh solvent to remove the excess surfactant before dissolving the nanoparticles with aqua regia. An AA sample of 50/50% Au/Fe feed composition nanoparticles captured in thiol-amine solution was prepared with the filtration and washing procedure. The composition of the nanoparticles was found to improve significantly, yielding a composition of 42% Au and 58% Fe. AA analysis of Au—Fe nanoparticles separated from the organic capture solution using a magnet should also give reliable particle compositions. Magnetic separation of the particles is able to separate the particles from excess surfactants and no undissolved solids are seen when the dried particles are dissolved in acid solution.

It was further found that particle composition of the phosphine captured and citrate captured nanoparticles varies linearly with the feed composition. Unlike the situation with organic captured nanoparticles, there is no surfactant residue present when the nanoparticles captured in water are dissolved with aqua regia. However, the Au—Fe nanoparticle composition is not always the same for the same feed composition. This may be caused by a shift in the actual feed composition in the crucible due to reusing crucibles with leftover feed from previous runs. It is observed that DACS runs using old crucibles tend to yield particles that are richer in gold for the same Au/Fe feed composition. This suggests that there could be some iron-rich residue in the reused crucible, which could have lowered the arc temperature and shifted the equilibrium state towards forming particles with higher gold fraction. This composition variation may also be caused by variation in the condition of the generated plasma arc and thus the temperature of the arc.

The particles have higher Fe compositions than predicted by Raoult's law at 3000K. The Raoult's law prediction of particle composition calculated at temperatures 4000K and above seems to correlate better with the experimental results. There is a possibility that the actual arc temperatures are higher than expected. It is also plausible that the arc temperature changes with the composition in the melt, i.e. increases with increasing gold composition. Therefore, the Au—Fe particle compositions across the composition range may not be correlated by Raoult's law calculated at only one temperature.

The particle composition also seems to depend on the purity of the feed. Runs with only 99+% pure iron were found to have higher gold fractions than expected. It is speculated that somehow the iron purity affects the partial pressure of iron in the arc and decreases the iron composition in these particles. Iron less than 99.9% pure may have relatively high amount of impurities such as oxides, silicon, cobalt, or nickel, which could potentially decrease iron solubility in gold and the vapor pressure of iron.

Example VI

Magnetic Properties of DACS Synthesized Au—Fe Nanoparticles

Fe nanoparticles synthesized using a multiple expansion cluster source (MECS) and captured with organic surfactants were found to oxidize to α-Fe$_2$O$_3$ (rust) and lose their magnetic properties after a few hours in solution. The Au—Fe nanoparticles synthesized in the present examples, however, retain their magnetic properties after several months in solution whether they are captured in organic or aqueous solution. A coarse check on the magnetization of DACS synthesized Au—Fe nanoparticles can be done by placing a permanent magnet on the side of the sample bottle to see if the particles respond to the magnet. TEM analysis has shown that the Au and Fe atoms in the DACS nanoparticles do not phase segregate into obvious Au-rich and Fe-rich phases. Therefore, it is speculated that the iron atoms are isolated in the core of the particles and protected by Au from oxidation. In order to quantify the magnetization of the Au—Fe nanoparticles, the magnetic characteristics of the DACS nanoparticles were measured using the SQUID magnetometer in Professor Majetich's laboratory at Carnegie Mellon University.

Magnetization of Organic Captured and Aqueous Captured Au—Fe Nanoparticles

Magnetic measurements on the Au—Fe nanoparticles captured in organic solution using the mixed thiol-amine surfactants and in water solution using sodium citrate show that they are superparamagnetic with very small coercivity and remanence. The Au—Fe nanoparticles also exhibit a relatively large saturation magnetization. Magnetization curves were made of a sample of Au—Fe nanoparticles captured in organic solution with an average particle composition of 48/52% Au/Fe and a sample of Au—Fe nanoparticles captured in water solution with an average particle composition of 44/56% Au/Fe. (The Au—Fe nanoparticles stabilized by citrate in water were transferred into organic solution before being captured for magnetic measurements.) The magnetic measurements were performed at 100K and 293K within the magnetic field (H) range of ±50,000Oe. As expected, the magnetization of the particles is higher at lower temperature. It was found that the nanoparticles initially captured in water have a lower magnetization than the nanoparticles captured in organic solution.

Table 2 summarizes the magnetic and physical properties of Au—Fe nanoparticles captured in organic solution, and Table 3 summarizes the magnetic and physical properties of Au—Fe nanoparticles captured in citrate solution. The small particle sizes of water-captured nanoparticles might be the reason for the lower saturation magnetization of water-captured nanoparticles as compared to organic captured nanoparticles. At a given composition, the fraction of iron atoms on the particle surface of a small particle is higher than that of a bigger particle. Since the nanoparticles captured in water are mostly below 8 nm in diameter, the ratio of surface iron atoms to core iron atoms is expected to be significantly high for these particles. As the surface iron atoms are predicted to be mostly oxidized, the ratio of oxidized iron atoms to unoxidized iron atoms within the small particles captured in water would be expected to be greater than that in the larger particles captured in organic solution.

Based on the saturation magnetization values measured in these experiments, the sample weight, and the particle composition, the magnetic moment per iron atom of the nanoparticles was calculated and plotted with respect to the average atomic fraction of iron in the particles. The saturation magnetic moment of the organic captured Au—Fe nanoparticles is roughly proportional to the iron atomic fraction within the particles. However, the magnetic moment per iron atom increases with increasing atomic fraction of iron instead of staying constant. Perhaps, in an iron-rich particle, the iron atoms coalesce into small atomic clusters, which yield a higher average spin moment. In a gold-rich particle, the iron atoms may be more highly dispersed among the gold atoms, thus lowering the average spin moment per iron atom.

Unlike the organic captured Au—Fe nanoparticles, the magnetic moment per iron atom of the water captured Au—Fe nanoparticles seems to decrease with increasing atomic fraction of Fe. This decrease may be caused by the fact that the water-captured nanoparticles are smaller in size than the organic captured nanoparticles and are therefore more sensitive to oxidation. Although sample A in Table 3 had a slightly higher average particle size than sample B, the iron atomic fraction was much higher for sample A. At this high iron fraction and small particle size, the iron atoms might not be effectively protected from oxidation, thus lowering the magnetic moment per iron atom of the particles. However, there is also the possibility that a composition limit is reached, whereby further increase in iron atomic composition beyond ~52% will significantly increase the fraction of oxidized iron atoms in the particles regardless of whether the particles are captured in organic or aqueous solution. Further investigation on the magnetization of Au—Fe nanoparticles with iron compositions above 52% up to 70% needs to be done to determine optimum Au/Fe ratio for maximum particle magnetization.

TABLE 2

Magnetic and physical properties of Au—Fe nanoparticles captured using mixed thiol-amine surfactants in mesitylene.

| Au—Fe Samples | Particle Molar Composition | | Sample Weight (mg) | Size Range | Average Particle Size | Coercivity, Hc (Oe) | | Remanence, Mr (emu/g) | | Saturation Magnetization Ms (emu/g) | |
|---|---|---|---|---|---|---|---|---|---|---|---|
| | Au | Fe | | | | 100K | 293K | 100K | 293K | 100K | 293K |
| 1 | 0.48 | 0.52 | 8.5 | 4–50 nm | 10 nm | 50 | 20 | 2.30 | 0.90 | 25.5 | 22.5 |
| 2 | 0.54 | 0.46 | 17.0 | 4–60 nm | 11 nm | 25 | 20 | 0.44 | 0.23 | 11.0 | 7.8 |
| 3 | 0.56 | 0.44 | 2.0 | 4–50 nm | 7 nm | 112 | 72 | 0.86 | 0.57 | 9.5 | 8.1 |
| 4 | 0.64 | 0.36 | 12.0 | 3–50 nm | 6 nm | 34 | 10 | 0.14 | 0.04 | 2.4 | 2.1 |

TABLE 3

Properties of Au–Fe nanoparticles captured using sodium citrate in water.

| Au—Fe Samples | Particle Molar Composition | | Sample Weight (mg) | Size Range | Average Particle Size | Coercivity, Hc (Oe) | | Remanence, Mr (emu/g) | | Saturation Magnetization Ms (emu/g) | |
|---|---|---|---|---|---|---|---|---|---|---|---|
| | Au | Fe | | | | 100K | 293K | 100K | 293K | 100K | 293K |
| A | 0.44 | 0.56 | 2.1 | 4–20 nm | 6 nm | 35 | 7 | 6.20 | 0.68 | 9.7 | 8.2 |
| B | 0.56 | 0.44 | 2.1 | 3–35 nm | 5 nm | 45 | 30 | 6.10 | 2.64 | 10.0 | 8.2 |

Based on the long-term magnetic stability of the DACS nanoparticles, the iron atoms in the particles appear to be successfully protected from oxidation. However, the water captured Au—Fe nanoparticles have a lower saturation magnetization than the organic captured Au—Fe nanoparticles, and the magnetic moment per iron atom within the nanoparticles is much lower than the magnetic moment per iron atom in bulk iron, which is 2.2 $\mu_B$/Fe atom, or in dilute Fe/Au bulk alloys, which is 2.6 $\mu_B$/Fe atom. The iron atoms on the surface of the particles are most probably oxidized to $\alpha$-$Fe_2O_3$ (haematite) and this may be the reason that the magnetic moment per iron atom in the particles is less than expected. There is also the possibility that some or all of the iron in the particles could be partially oxidized to a metastable magnetic state ($Fe_3O_4$ and $\gamma$-$Fe_2O_3$). Further investigation on the iron oxidation state, particle spin domains and the electron coupling between gold and iron needs to be done to better understand the magnetic behavior of these Au—Fe nanoparticles.

Variation in the Properties of DACS Au—Fe Nanoparticles

Tables 4 and 5 compare the properties of the Au—Fe nanoparticles captured by a permanent magnet (0.3T) for magnetic measurements to the properties of the Au—Fe nanoparticles that remained in the solution, i.e. were not drawn out of the solution by the magnet. The nanoparticles not magnetically captured usually constitute about 10–20% of the total nanoparticle sample.

AA analysis of the Au—Fe nanoparticles not separated by the magnet shows that these nanoparticles have a lower gold content than the nanoparticles separated from solution by the magnet. Therefore, DACS Au—Fe nanoparticles do exhibit a composition variation from one particle to another. Surprisingly, the nanoparticles that are not separated by the magnet are richer in iron than those that are separated. It is speculated that these Au—Fe nanoparticles with lower gold content have low magnetic moments or simply are not magnetic due to a higher iron content on the particle surface or phase segregation within the particle to gold-rich and iron-rich regimes. Either case would expose more of the iron atoms to oxidation. Although Au—Fe particles that are very rich in iron have a tendency to form heterogeneous particles with an iron oxide layer surrounding a gold core, such structure was not obvious in the TEM micrographs of the Au—Fe nanoparticles not separated by the magnet. However, two-phase structures such as a dark hemisphere attaching to a lighter hemisphere were at times seen. When the gold and iron atoms phase segregate to form iron-rich or gold-rich phases, the iron atoms are most likely to be oxidized and lose their magnetic characteristics.

In addition to being richer in their iron content, the organic captured Au—Fe nanoparticles not separated by the magnet are generally smaller in size than those that are separated by the magnet. This is to be expected as gold atoms are known to have greater affinity towards each other than iron atoms do. Thus, particles with a higher fraction of gold atoms on their surface will tend to coalesce to produce larger particles. Also, since the fraction of protected core iron atoms decreases with decreasing particle size, the magnetic moment of a small particle is likely to be significantly lower than that of a bigger particle with the same composition. Therefore, nanoparticles with small diameters and high iron content are most likely to have low specific magnetic moments. Unlike the organic captured Au—Fe nanoparticles, the water captured Au—Fe nanoparticles not drawn to the magnet have the same average particle size as the ones drawn to the magnet. Since the water captured nanoparticles are generally very small (average diameter below 8 nm), the magnetic properties of these nanoparticles are largely dependent on the particle composition and how the gold and iron atoms are distributed within a particle.

TABLE 4

Physical properties of Au—Fe nanoparticles captured in organic solution with respect to whether the particles are captured by a permanent magnet or not.

| | Captured | | | | Not Captured | | | |
|---|---|---|---|---|---|---|---|---|
| Au—Fe Samples | Particle Composition | | Particle Size | Average Size | Particle Composition | | Particle Size | Average Size |
| | Au | Fe | | | Au | Fe | | |
| 1 | 0.48 | 0.52 | 4–50 nm | 10 nm | 0.41 | 0.59 | 4–12 nm | 8 nm |
| 3 | 0.56 | 0.44 | 4–50 nm | 7 nm | 0.44 | 0.56 | 3–24 nm | 5 nm |
| 4 | 0.64 | 0.36 | 3–50 nm | 6 nm | 0.61 | 0.39 | 3–30 nm | 5.5 nm |

TABLE 5

Particle composition of Au—Fe nanoparticles originally captured in citrate/water solution with respect to whether the particles are captured by a permanent magnet or not.

| | | Particle Composition (mol/mol) | |
|---|---|---|---|
| | | Au | Fe |
| Au—Fe Sample 1: | In Bulk Solution | 0.36 | 0.64 |
| | Captured | 0.44 | 0.56 |
| | Not Captured | 0.34 | 0.66 |
| Au—Fe Sample 2: | In Bulk Solution | 0.46 | 0.54 |
| | Captured | 0.56 | 0.44 |
| | Not Captured | 0.32 | 0.68 |

Example VII

Preparation of Fe/Au Nanoparticles

The Fe(50)/Au(50) nanoparticles whose magnetization curves are shown in FIG. 6 were prepared using the Distributed Arc Cluster Source (DACS) shown in FIG. 1. Gold and iron metals with 99.9% purity were purchased from Alfa Aesar (Ward Hill, Mass.). The DACS has a positively biased carbon rod which supports the tungsten feed crucible, and a negatively biased tungsten rod of 0.06 inches diameter which provides a sharp point for effective plasma arc generation. During the operation, argon gas is continuously fed from the bottom of the DACS column to serve as a carrier gas for the metal vapor. Argon also serves as a precursor for arc generation.

The positively charged feed crucible was raised until the metal charge in the crucible comes in contact with the negatively charged tungsten rod. The electrical spark that results ionized the argon gas and a plasma arc formed between the tungsten rod and the metal charge in the crucible. The crucible is then lowered a fixed distance to establish a predetermined arc voltage drop. The plasma arc has a temperature as high as 4000 K and provides the heat necessary to evaporate the metal charge. After arc initiation, the arc was maintained primarily by the ionized metal vapor from the feed rather than argon. The temperature outside of the plasma arc is much lower than the temperature in the arc itself. Gas phase nanoparticles were formed when the metal vapor is swept upstream by the argon gas. Helium quench gas at room temperature was mixed with the flow from the arc region and this further cooled the nanoparticles.

The aerosol stream from the DACS was bubbled into a 130 ml capacity capture cell made of Pyrex glass (FIG. 2). The capture cell is a 19" long cylinder with a 1.5" diameter and contains 6 Teflon baffles, which provide good liquid-gas contact. The capture cell contained a solution of 4.2 mmol dodecanethiol, 0.27 mmol dodecylamine, and 0.17 mmol didecylamine in 120 ml of mesitylene. All chemicals were purchased from Aldrich. The mesitylene was 97% pure and the surfactant molecules were all 98% pure.

After a run of approximately 15 minutes the DACS was shut down and the solution in the capture cell now containing Fe/Au nanoparticles in suspension was allowed to settle for an hour and then was transferred into a separatory flask. The solution was allowed to flow through a Tygon tube nominally 0.25" in diameter past a 0.3 T permanent magnet, which caused the entrained Fe/Au nanoparticles to collect on the wall of the tube at the location of the magnet. This bulk sample was air dried and weighed. It was then mixed with epoxy and placed in a plastic straw for insertion into a Quantum Design MPMS SQUID Magnetometer for the magnetization measurements. The magnetization curves were obtained in the laboratory of Professor Sarah Majetich at Carnegie Mellon University.

Separate measurements on this sample yielded an average particle size of 10 nm and a composition of Fe(50)/Au(50).

The complete disclosures of all patents, patent applications including provisional patent applications, publications, and electronically available material (e.g., GenBank amino acid and nucleotide sequence submissions) cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

---

What is claimed is:

1. A superparamagnetic nanoparticle comprising Fe atoms and Au atoms distributed in a solid solution with no observable segregation into Fe-rich or Au-rich phases or regions.

2. The nanoparticle of claim 1, wherein the nanoparticle is equiaxed with spherical morphology.

3. The nanoparticle of claim 1, wherein the nanoparticle is characterized by a uniform volume magnetization.

4. The nanoparticle of claim 1, wherein the nanoparticle has a saturation magnetization proportional to the number of Fe atoms in the nanoparticle.

5. The nanoparticle of any of claims 1 to 4 wherein the diameter of the nanoparticle is about 5 nm to about 50 nm.

6. The nanoparticle of any of claims 1 to 4 consisting of Fe atoms and Au atoms, wherein the Fe atom/Au atom ration does not exceed about 1:1, i.e., Fe(50)/Au(50).

7. The nanoparticle of any of claims 1 to 4 wherein Fe atoms in the interior of the nanoparticle are protected from oxidation.

8. The nanoparticle of any of claims 1 to 4 comprising a metal core comprising the Fe atoms and the Au atoms, and a plurality of organic molecules linked to the surface of the metal core.

9. The nanoparticle of claim 8 wherein the organic molecules are selected so as to render the nanoparticle soluble in an organic solvent.

10. The nanoparticle of claim 8 wherein the organic molecules are selected so as to render the nanoparticle soluble in an aqueous environment.

11. The nanoparticle of claim 8 wherein the organic molecule comprises a hydrophobic polymer or a hydrophilic polymer.

12. The nanoparticle of claim 8 wherein the organic molecules are selected from the group consisting of a nucleic acid, a protein, a carbohydrate and a lipid.

13. The nanoparticle of claim 8 wherein the organic molecules comprise a sulfur atom, and wherein the organic molecules are linked to the surface of the metal core through an interaction between the Au atoms on the surface of the metal core and the sulfur atoms of the organic molecules.

14. The nanoparticle of claim 13 comprising a plurality of first organic molecules comprising hydrophobic or hydrophilic polymers comprising the sulfur atoms, and further comprising a plurality of second organic molecules covalently liked to the first organic molecules, such that the first organic molecules function as a chemical linker that indirectly links the second organic molecules to the surface of the metal core.

15. The nanoparticle of claim 14 wherein the second organic molecules are selected from the group consisting of a nucleic acid, a protein, a carbohydrate and a lipid.

16. A method for making a plurality of superparamagnetic nanoparticles, the method comprising:

evaporating a metal comprising Fe atoms and Au atoms using an atmospheric pressure direct current arc discharge to yield a metal vapor;

contacting the metal vapor with a forced convective flow of argon gas to control particle nucleation and growth, yielding solid metal nanoparticles such that the Fe atoms and the Au atoms are distributed in a solid solution with no observable segregation into Fe-rich or Au-rich phases or regions;

contacting the nanoparticles with a forced convective flow of helium or nitrogen gas to yield cooled nanoparticles; and bubbling the cooled nanoparticles through a liquid to yield a colloidal suspension of superparamagnetic nanoparticles.

17. The method of claim 16 wherein the liquid is aqueous sodium citrate.

18. The method of claim 16 wherein the liquid is an organic solvent.

19. The method of claim 16 wherein the liquid is mesitylene.

20. The method of claim 16 wherein the nanoparticles consist of Fe atoms and Au atoms, and wherein the Fe atom/Au atom ratio does not exceed about 1:1, i.e., Fe(50)/Au(50).

21. The method of claim 16 wherein the magnetic moment of the nanoparticles is proportional to the number of Fe atoms in the nanoparticles.

22. The method of claim 16 further comprising controlling the composition of the nanoparticles by controlling the composition of the metal charge of Fe atoms and Au atoms.

23. The method of claim 16 further comprising controlling the mean size of the particles by controlling the metal evaporation rate, the argon flow rate, or both.

24. The method of claim 16 wherein the rate of production of nanoparticles is on the order of grams per hour.

25. The method of claim 16 further comprising linking a plurality of organic molecules to the surface of the superparamagnetic nanoparticle.

* * * * *

UNITED STATES PATENT AND TRADEMARK OFFICE
CERTIFICATE OF CORRECTION

PATENT NO.        : 7,186,398 B2
APPLICATION NO.   : 10/373609
DATED             : March 6, 2007
INVENTOR(S)       : Andres et al.

Page 1 of 1

It is certified that error appears in the above-identified patent and that said Letters Patent is hereby corrected as shown below:

At column 29, line 25, in Claim 6, delete the word "ration" and insert -- ratio --.

Signed and Sealed this

Sixth Day of November, 2007

JON W. DUDAS
*Director of the United States Patent and Trademark Office*

SEQUENCE LISTING

```
<160> NUMBER OF SEQ ID NOS: 3

<210> SEQ ID NO 1
<211> LENGTH: 15
<212> TYPE: DNA
<213> ORGANISM: Artificial Sequence
<220> FEATURE:
<223> OTHER INFORMATION: misc_binding site using 5' alkyl thiolated
      -CH2)6SH

<400> SEQUENCE: 1
gtcagtccgt cagtc                                                   15

<210> SEQ ID NO 2
<211> LENGTH: 15
<212> TYPE: DNA
<213> ORGANISM: Artificial Sequence
<220> FEATURE:
<223> OTHER INFORMATION: misc-binding site using a 3" alkyl tholate of
      -(CH2)6SH

<400> SEQUENCE: 2
atcctcaact ctccg                                                   15

<210> SEQ ID NO 3
<211> LENGTH: 24
<212> TYPE: DNA
<213> ORGANISM: Artificial Sequence
```

```
-continued

<220> FEATURE:
<223> OTHER INFORMATION: Linker DNA substrate

<400> SEQUENCE: 3
agagttgagc atgactgacg gact                                              24
```